(12) United States Patent
Barde et al.

(10) Patent No.: US 11,121,422 B2
(45) Date of Patent: Sep. 14, 2021

(54) FLUORINATED IONIC LIQUIDS WITH HIGH OXYGEN SOLUBILITY FOR METAL-AIR BATTERIES

(71) Applicants: TOYOTA MOTOR EUROPE, Brussels (BE); KATHOLIEKE UNIVERSITEIT LEUVEN, K.U. LEUVEN R&D, Leuven (BE)

(72) Inventors: Fanny Barde, Brussels (BE); Gijs Vanhoutte, Aarschot (BE); Sandra Dorota Hojniak-Thyssen, Leuven (BE); Koen Binnemans, Zele (BE); Jan Fransaer, Leefdaal (BE)

(73) Assignees: TOYOTA MOTOR EUROPE, Brussels (BE); KATHOLIEKE UNIVERSITEIT LEUVEN, K.U. LEUVEN R&D, Leuven (BE)

( * ) Notice: Subject to any disclaimer, the term of this patent is extended or adjusted under 35 U.S.C. 154(b) by 162 days.

(21) Appl. No.: 16/326,662

(22) PCT Filed: Aug. 16, 2016

(86) PCT No.: PCT/EP2016/069442
§ 371 (c)(1),
(2) Date: Feb. 19, 2019

(87) PCT Pub. No.: WO2018/033200
PCT Pub. Date: Feb. 22, 2018

(65) Prior Publication Data
US 2019/0190104 A1 Jun. 20, 2019

(51) Int. Cl.
*H01M 12/02* (2006.01)
*H01M 12/08* (2006.01)
(Continued)

(52) U.S. Cl.
CPC .......... *H01M 12/02* (2013.01); *C07C 217/08* (2013.01); *C07D 295/088* (2013.01);
(Continued)

(58) Field of Classification Search
CPC ..... H01M 12/02; H01M 12/08; C07C 217/08; C07D 295/088
See application file for complete search history.

(56) References Cited

U.S. PATENT DOCUMENTS 4,873,020 A 10/1989 Muggli
7,282,295 B2 10/2007 Visco et al.
(Continued)

OTHER PUBLICATIONS

Nakamoto et al., "Ether-functionalized Ionic Liquid Electrolytes for Lithium-Air Batteries", Journal of Power Sources, vol. 243, pp. 19-23. 2013. (Year: 2013).*
(Continued)

*Primary Examiner* — Matthew J Merkling
(74) *Attorney, Agent, or Firm* — Oliff PLC

(57) ABSTRACT

Ionic compounds containing an anion, and a cation having the following structural formula (1):

$$R^1R^2R^3N^+\text{-(linker}^1\text{)-O-(linker}^2\text{)-(FC)} \quad (1)$$

wherein: $R^1$ and $R^2$ either linear or branched alkyl groups or together form a N-heterocylic ring with the nitrogen atom to which they are joined; $R^3$ is linear or branched alkyl group; linker$^1$ and linker$^2$ are alkylene chains or polyether chains; and the group FC is a fluorinated alkyl group, as well as an electrolyte material comprising such an ionic compound and a metal salt, and metal-air batteries using such an electrolyte material. The invention also relates to a metal-air battery containing an electrolyte material, wherein the electrolyte material comprises at least one ionic compound and a metal
(Continued)

salt, and wherein at least one ionic compound contains an anion $C_nF_{2n+1}COO^-$ or $C_nF_{2n+1}SO_3^-$, where in each case n is at least 1 and at most 10.

12 Claims, 9 Drawing Sheets

(51) Int. Cl.
    *C07C 217/08*      (2006.01)
    *C07D 295/088*      (2006.01)

(52) U.S. Cl.
    CPC .... *H01M 12/08* (2013.01); *H01M 2300/0025* (2013.01); *H01M 2300/0034* (2013.01); *Y02E 60/10* (2013.01)

(56) References Cited

U.S. PATENT DOCUMENTS

| | | | |
|---|---|---|---|
| 7,491,458 B2 | 2/2009 | Visco et al. | |
| 2006/0094882 A1* | 5/2006 | Umemoto | C07C 381/12 546/347 |
| 2007/0275326 A1* | 11/2007 | Hatakeyama | G03F 7/2041 430/270.1 |
| 2012/0107697 A1* | 5/2012 | Roh | H01M 10/4235 429/330 |
| 2012/0266907 A1 | 10/2012 | Chan | |
| 2013/0115529 A1 | 5/2013 | Zhang et al. | |
| 2013/0149596 A1* | 6/2013 | Shiflett | H01M 2/02 429/163 |
| 2013/0235509 A1* | 9/2013 | Ruoff | H01M 4/133 361/502 |
| 2014/0200220 A1* | 7/2014 | Maisch | A01N 43/90 514/251 |
| 2014/0287640 A1* | 9/2014 | Hariprakasha | C07D 233/61 442/140 |
| 2015/0364801 A1* | 12/2015 | Wijaya | H01M 4/133 429/403 |

OTHER PUBLICATIONS

Feb. 3, 2017 International Search Report issued in International Patent Application No. PCT/EP2016/069442.
Feb. 3, 2017 Written Opinion of the International Searching Authority issued in International Application No. PCT/EP2016/069442.

* cited by examiner

FLUORINATED IONIC LIQUIDS WITH HIGH OXYGEN SOLUBILITY FOR METAL-AIR BATTERIES

FIELD OF THE INVENTION

The present invention relates to ionic compounds that can be used as ionic liquid-type electrolytes in metal-air batteries such as lithium-air batteries.

BACKGROUND ART

Metal-air batteries are being actively investigated as energy storage devices. Lithium-air batteries, having a high energy density, are of particular interest for electrical vehicles. In developing appropriate electrolytes for such batteries, attention must be paid to the stability of the electrolyte to $O_2$-derived radical species. Low volatility is an advantage for open-type batteries, but high viscosity may reduce battery performance.

Nakamoto et al. in *J. Power Sources*, 243 (2013), 19-21, describe a functionalized ionic liquid for Li-air batteries. Various cations, and as counterion bis(trifluoromethanesulfonyl)amide (TFSA) anion, were investigated:

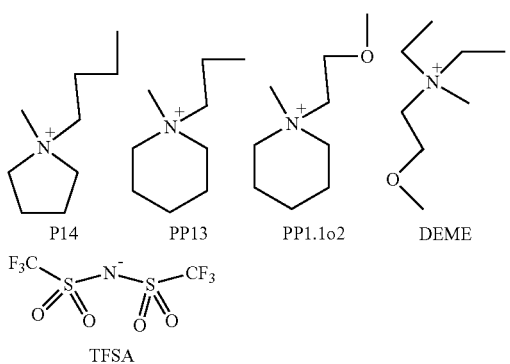

Elia et al. in *Nanoletters*, 2014, 14, 6572-6577, describe a lithium-air battery using an ionic liquid-based electrolyte, specifically bis(trifluoromethanesulfonyl)imide-lithium LiTFSI (also called $LiTf_2N$) with cation $Pr14^+$ (also called $BMPyr^+$), provided as the TFSI salt of N-butyl-N-methylpyrrolidinium.

S. Monaco et al. in *Electrochemica Acta* 82 (2012) 94-104, provided an electrochemical study of oxygen reduction in pyrrolidinium-based ionic liquids for $Li/O_2$ batteries. The known fluorinated anions TFSI, BETI and IM14 were used in order to increase $O_2$ concentration in the electrolyte.

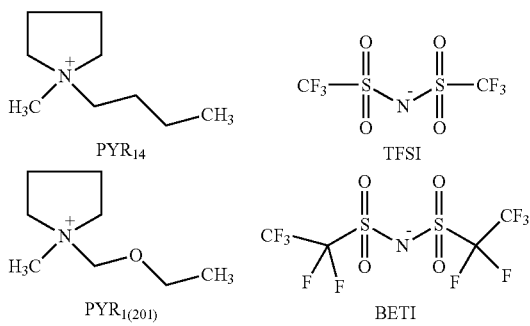

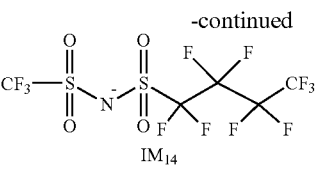

S. Monaco et al. in *Journal of Phys. Chem. Letters*, 2013, 4, 1379-1382, use $Pyr_{14}TFSI$: LiTFSI (9:1) as ionic liquid (IL) for $Li—O_2$ batteries.

M. Kar et al., in *Phys. Chem. Chem. Phys.* (PCCP), 2014, 16, 18658-18674, discuss ionic liquid electrolytes as a platform for rechargeable metal air batteries, in a review of room temperature ionic liquids (RTIL) and $O_2$ solubility.

A. B. Pereiro et al., in *ACS Sustainable Chem. Eng.* 2013, 1, 27-439, discuss fluorinated liquid liquids and their possible applications.

The use of fluorinated compounds as additives to electrolyte solvents has been described, for example in Yazami et al. "Perfluorocarbon Additive Behaviour on Lithium Oxygen Battery", Abstract MA2014-04 507 Session 6—Beyond Lithium Ion Posters—Jun. 11, 2014, 2014 ECS—The Electrochemical Society, http://ma.ecsdl.org/content/MA2014-04/3/507.abstract. Here, perfluorocarbon (PFC) is added to ether. This was taught to improve the discharge voltage significantly up to 200 mV for 20% PFC addition in 0.1 M $LiClO_4$ in tetraglyme (TEGDME) electrolyte. This technology means however that ether-based organic solvents are used that present intrinsically a certain volatility.

In US 2012/266907, electrodes are disclosed that comprise a fluorinated or metalloprotein oxygen dissolution enhancer for enhancing dissolution of oxygen in the solvent, for use in a metal-air battery. The fluorinated compound is for example a fluorinated polymer, or a fluorinated ether with formulae $C_{m+n}H_{2m+1}F_{2n+1}O$, or fluorinated ester with formulae $C_{m+n}H_{2m+1}F_{2n+1}C(O)O$, or fluorinated carbonate $C_{m+n}H_{2m+1}F_{2n+1}CH(CO_3)$ or fluorocarbon $C_nF_m$ or $C_nF_pH_q$. Here therefore fluorinated compounds are used as additive, they are not part of the ionic liquid ion pair as such.

US 2013/0115529 discloses fluorinated compounds used as co-solvents for non-aqueous electrolytes for metal air battery cells. The other co-solvent is preferably taken from the family of carbonates, ethers, nitriles, esters, sulfites and combinations thereof. The fluorinated compounds used are fluorinated phosphorus compounds, notably alkyl phosphates and phosphazenes, having possibly functional groups containing fluorine (such as trifluoromethyl). Here therefore fluorinated compounds act as additives, not part of the ionic liquid ion pair as such, and miscibility problems may arise when using co-solvents.

Nishikami et al., *J. Mater. Chem. A*, 2015, 3, 10845-10850 describe $O_2$-enriched electrolytes based on perfluorochemicals for high capacity lithium oxygen batteries. Electrolytes highly enriched with oxygen for lithium-oxygen ($Li—O_2$) batteries were prepared by combining perfluorohexyl bromide ($BrC_6F_{13}$) as an oxygen-uptake perfluorochemical (PFC) medium with lithium perfluorooctane sulfonate (LiPFOS) as a perfluoro-surfactant and a supporting electrolyte. As a result the $O_2$ solubility of 1M LiTFSI and 2M LiFPOS TEGDME electrolyte solutions were 8.4 and 8.9 mg/L, respectively and was enhanced up to 13 mg/L for a 60 wt % $BrC_6F_{13}$-containing LiFPOS electrolyte solution. The use of ether-based organic solvents presents volatility issues however, and there may be miscibility problems when using co-solvent.

Y. Wang et al., *EES* 2011, 4, 3697, doi 10.1039/c1ee01556g, used perfluorotributylamine (FTBA) as additive in $LiPF_6$/PC electrolyte to increase $O_2$ solubility. FTBA does not dissolve in PC carbonate, thus only 0.5 wt % was added and dispersed through ultrasonic emulsification. Again, issues of electrolyte solvent volatility, and miscibility, may arise.

WO 2014/133466 discloses an electrolyte for metal air battery composed of: an ionic liquid (IL), a bridging solvent (organic solvent), a fluorinated carbon compounds and a metal salt. Here therefore fluorinated compounds act as additives, not part of the ionic liquid ion pair as such, and miscibility problems may arise when using co-solvents. The presence of volatile compounds may also be a disadvantage.

It is desirable in view of the state of the art to provide new ionic liquids that can be used as electrolytes and/or solvents in air battery and/or oxygen battery applications. High oxygen solubility is desirable in these applications, which leads to higher performances in terms of higher discharge capacity, and higher rate capability of the air (oxygen) battery using such an electrolyte. In addition, low volatility is required, allowing electrolyte systems to be used in an open or half-open system, or flow gas system. Ionic liquids stable against $O_2$ radicals are desired, as well as ones which are thermally stable and electrochemically stable in the potential window of interest for air battery. A generally hydrophobic character of ionic liquids in such applications may also be desirable.

SUMMARY OF THE INVENTION

The present invention has been developed with a view to solving one or more of the above-mentioned problems known in the art.

In one aspect, the present invention relates to an ionic compound containing an anion, and a cation having the following structural formula (1):

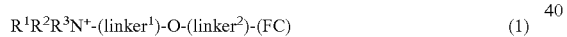

$R^1R^2R^3N^+$-(linker$^1$)-O-(linker$^2$)-(FC)    (1)

wherein:
 $R^1$ and $R^2$ either 1) are both C1-C6 linear or branched alkyl groups, preferably methyl or ethyl, or 2) together form a N-heterocylic ring with the nitrogen atom to which they are joined;
 $R^3$ is a C1-C6 linear or branched alkyl group, preferably methyl or ethyl;
 the linker$^1$ consists of: an alkylene chain —$(CH_2)_n$— wherein n≥1, or an chain of formula —$(CH_2$—O—$CH_2$-$)_p$ wherein p≥1;
 the linker$^2$ consists of an alkylene chain —$(CH_2)_m$— wherein m≥1, or an chain of formula —$(CH_2$—O—$CH_2$-$)_q$ wherein q≥1;
 the group FC is a fluorinated alkyl group of formula $C_aH_bF_c$ wherein b+c=2a+1, where c is at least 1 and at most 2a+1 and where a is at least 1 and at most 10.

In preferred ionic compounds of the invention whose cations are according to above general formula (1), $R^1R^2$ together form a ring with the nitrogen atom to which they are joined, and the ring is chosen from the group consisting of: pyrrolidine, piperidine, imidazole, pyridine and morpholine. For any of these ring types, one or more substituent groups may be present on the ring, the substituent groups being chosen from the group consisting of: halo, alkyl, and aryl groups. Naturally, since the nitrogen atom is this cationic part of the ionic compounds carries a positive charge, the rings in question are in the form of cations of the type: pyrrolidinium, piperidinium, imidazolium, pyridinium and morpholinium.

Most preferred N-heterocylic ring types for cations of formula (1) are pyrrolidine (pyrrolidinium) or piperidine (piperidinium).

Concerning preferred linker lengths, in linker$^1$, n is at most 10, preferably at most 2; and p is at most 5, preferably at most 1, and in linker$^2$, m is at most 10, preferably at most 1; and q is at most 5, preferably at most 1.

Preferred linker groups linker$^1$ and linker$^2$ consist of alkylene chains. The most preferred linker group linker$^1$ is ethylene —$CH_2$—$CH_2$—, and the most preferred linker group linker$^2$ is methylene —$CH_2$—.

It is preferred for the fluorinated alkyl group FC in the cation of above general formula (1) to be highly or indeed fully fluorinated, and so preferably c>b in the fluorinated alkyl group FC, more preferably c>2b, still more preferably c>3b, even more preferably c>5b.

In ionic compounds with a cation of above general formula (1), the anion is advantageously one or more chosen from the group consisting of: $C_nF_{2n+1}$—$SO_2$—N—$SO_2$—$C_mF_{2m+1}^-$, $PF_6^-$, $BF_4^-$, $C_nF_{2n+1}COO^-$ and $C_nF_{2n+1}SO_3^-$; where n and m are at least 1 and at most 10.

Particularly preferred ionic compounds of the invention include ones wherein the cation has one of the following structures:

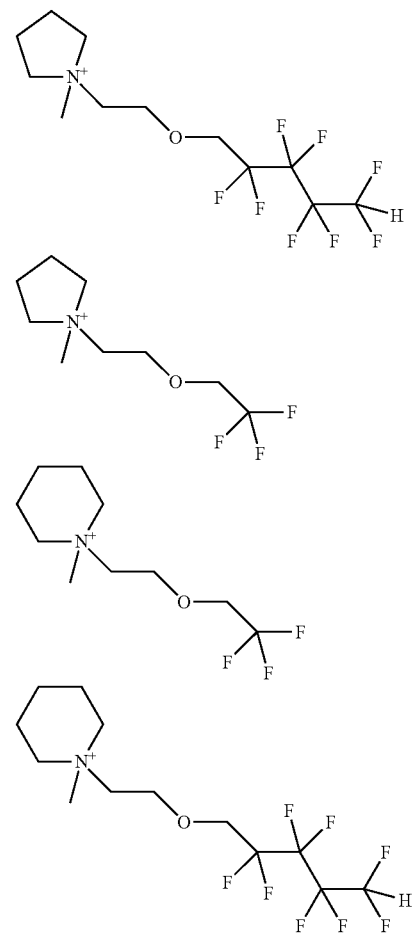

-continued

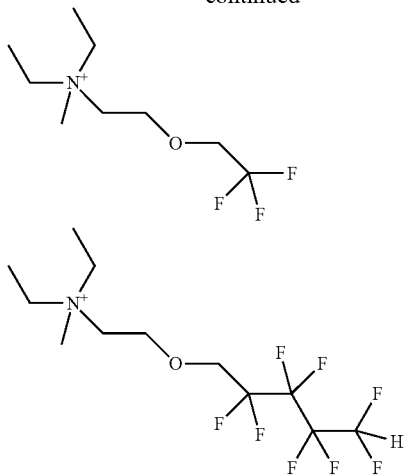

In another aspect, the present invention relates to an electrolyte material comprising an ionic compound as set out above, having a cation of above general formula (1), and a metal salt. The metal salt in the electrolyte material may advantageously be a lithium (Li) salt, such as LiFSI, LiTFSI, LiClO$_4$ and/or LiPF$_6$.

In another aspect, the present invention relates to a metal-air battery using an electrolyte material comprising an ionic compound as set out above, having a cation of above general formula (1), and a metal salt.

In another aspect, the present invention relates to an ionic compound having the following formula:

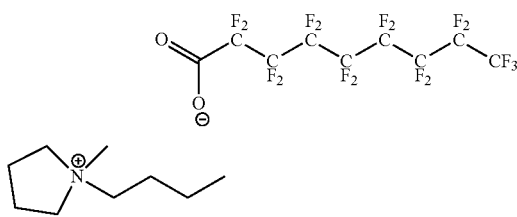

In another aspect, the present invention relates to a metal-air battery containing an electrolyte material, wherein the electrolyte material comprises at least one ionic compound and a metal salt, and wherein at least one ionic compound contains an anion $C_nF_{2n+1}COO^-$ or $C_nF_{2n+1}SO_3^-$, where in each case n is at least 1 and at most 10. It is envisaged in this metal-air battery of the present invention, the electrolyte material may comprise ionic compounds where a cation of above general formula (1) is combined with an anion $C_nF_{2n+1}COO^-$ or $C_nF_{2n+1}SO_3^-$, and/or the specific ionic compound above (N-methyl-butyl-pyrrolidinium $C_8F_{17}$—$CO_2^-$) and/or ionic compounds having other cations as counter ions for anions of formula $C_nF_{2n+1}COO^-$ or $C_nF_{2n+1}SO_3^-$.

As cation for anions of formula $C_nF_{2n+1}COO^-$ or $C_nF_{2n+1}SO_3^-$, possibilities include substituted or unsubstituted ring systems selected from the group consisting of: pyridinium, pyridazinium, pyrimidinium, pyrazinium, imidazolium, pyrazolium, thiazolium, oxazolium, triazolium, imidazolinium, methylpyrrolidinium, isothiazolium, isoxazolium, oxazolium, pyrrolium, and thiophenium. When substituted, the one or more substituent groups may be one or more of halo, alkyl, and aryl groups. Other possibilities for cations include tetrabutyl ammonium, tributylmethyl ammonium, tetrabutyl phosphonium, tetraethyl ammonium, N,N-dialkyl pyrrolidinium, trimethyl 2-hydroxyethyl ammonium, N,N'-dialkyl imidazolium, N-alkylpyridinium, 1-methyl-3-hexyl imadazolium and mixtures thereof.

In preferred embodiments, the cation acting as counter ion for anions of formula $C_nF_{2n+1}COO^-$ or $C_nF_{2n+1}SO_3^-$ in metal-air batteries according to this aspect of the invention contains a pyrrolidinium cation.

Ionic liquids according to the present invention, comprising cation and anion combinations as set out above in relation to the different aspects of the present invention, are considered to provide one or more of the following advantages:

High O$_2$ solubility (related to higher discharge capacity);
Low volatility related to the negligible vapor pressure of the ionic liquid and less chance to reach the state that the battery will die due to drying of electrolyte and components;
No miscibility problems such as encountered when fluorinated organic compounds (such as perfluorocarbons, denoted PFCs) are just added into electrolyte;
High thermal stability of the ionic liquids;
Low flammability of ionic liquid compared to classical organic solvents (DME, PC . . . ). As the vapor pressure of these ionic liquids is very low compared to molecular solvents, their flammability will be much better than most (if not all) molecular solvents;
Good stability of ILs versus O$_2^-$, important for metal-air (O$_2$) battery applications;
Good stability of ILs over a large potential window of interest for the target applications of metal-air (O$_2$) battery applications;
High ionic conductivities since ionic liquids are intrinsically conductive since they consist of ions;
Hydrophobicity: as the oxygen solubility was obtained by using either fluorinated cations, anions or both, the resulting ionic liquids are hydrophobic. This may be an advantage in the production process (of the electrolyte and or of the battery) where less contamination with water will occur. Also, in case of an open battery (air battery), this would present an advantage since possible moisture/humidity contained in the air will not be dissolved in the ILs thanks to their hydrophobicity properties.

was used as working electrode and a platinum coil as counter electrode. A real reference electrode was a silver wire in a glass tube with an acetonitrile solution of 0.01 M silver nitrate and 0.1 M tetrabutylammonium perchlorate, separated from the electrolyte using a glass frit. The scan rate was 100 mV s$^{-1}$ and each third cycle is shown.

Figure 1:
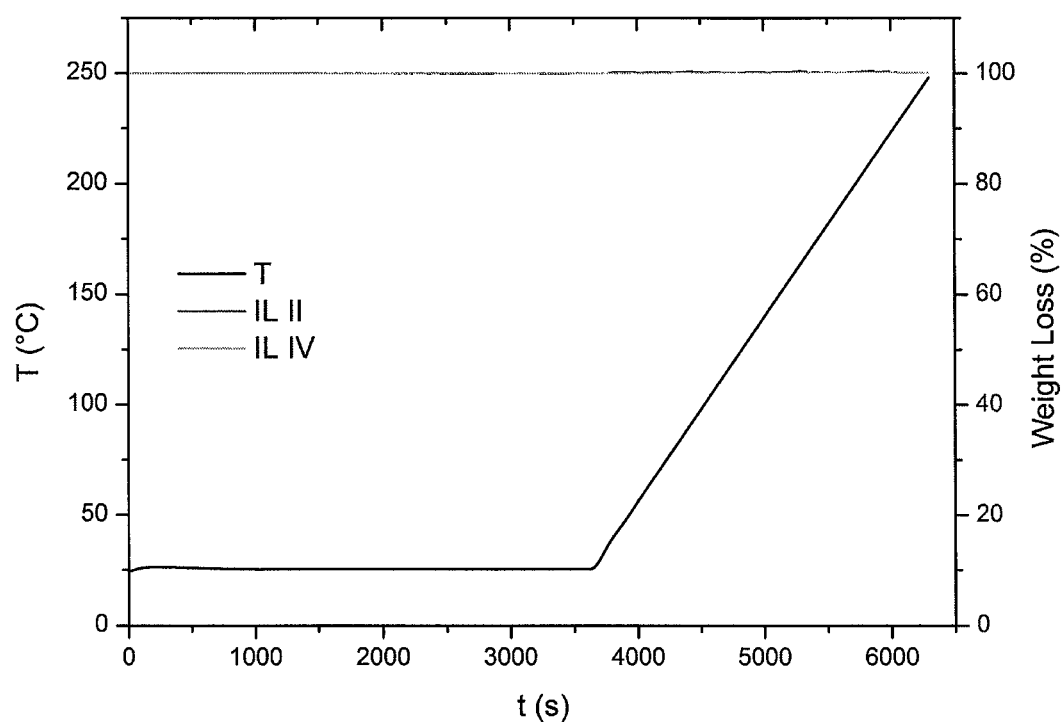
FIG. 1 shows thermogravimetric analysis of IL II and IV (ether functionalized pyrrolidinium cation family). The weight loss (volatility and/or decomposition) is measured in two steps, first at 25° C. for 1 h and subsequently the temperature is raised to 250° C. at 5° C./min. No weight loss was observed during the experiment and thus the ILs are stable and not volatile over the entire temperature range (25-250° C.).
Figure 2:
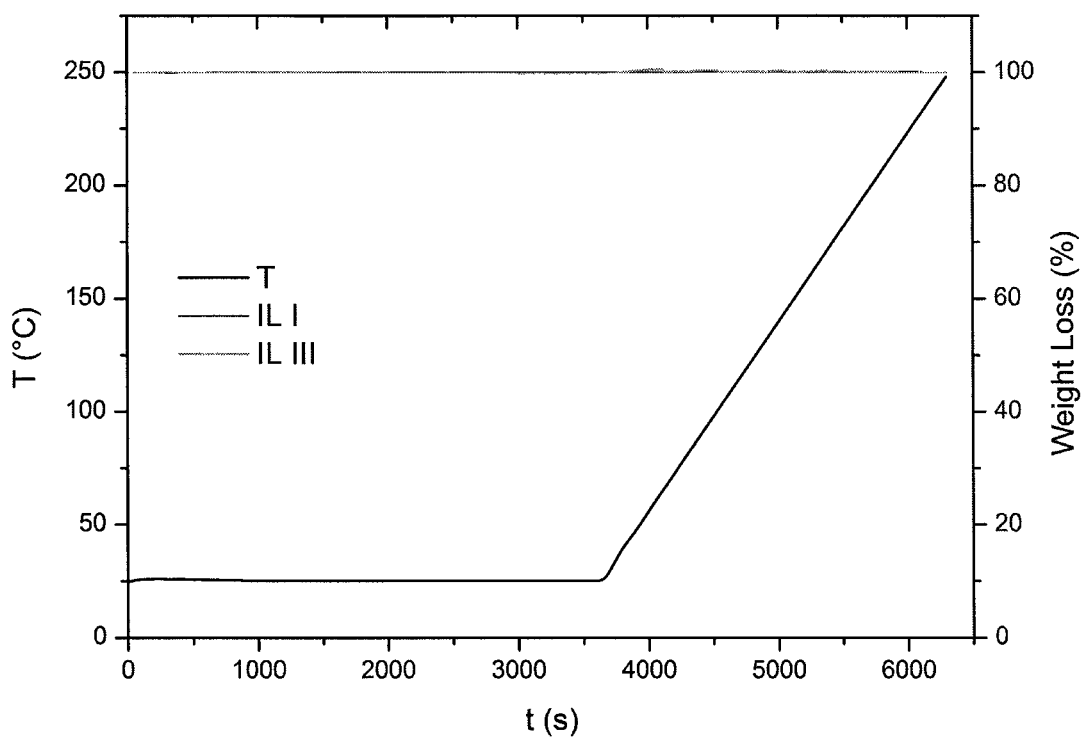
FIG. 2 and FIG. 3 show analogous thermogravimetric analyses of IL I and III (ether functionalized piperidinium cation family), and IL V and VI (ether functionalized quaternary ammonium cation family), respectively.
Figure 3:
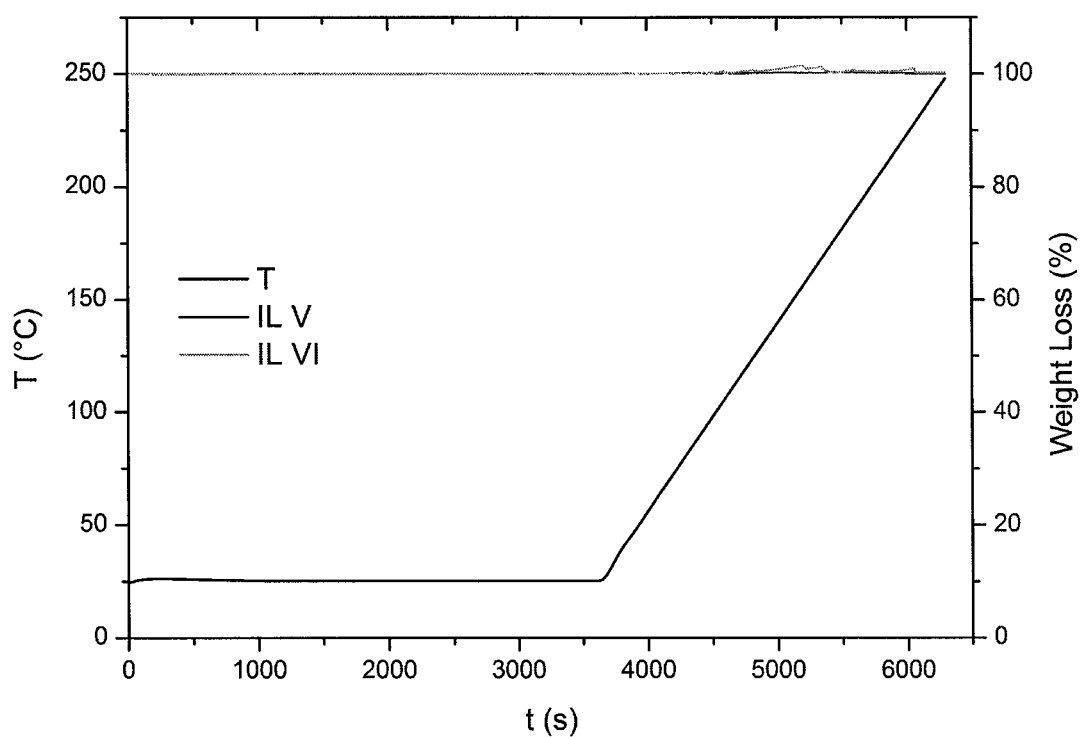
Figure 4:
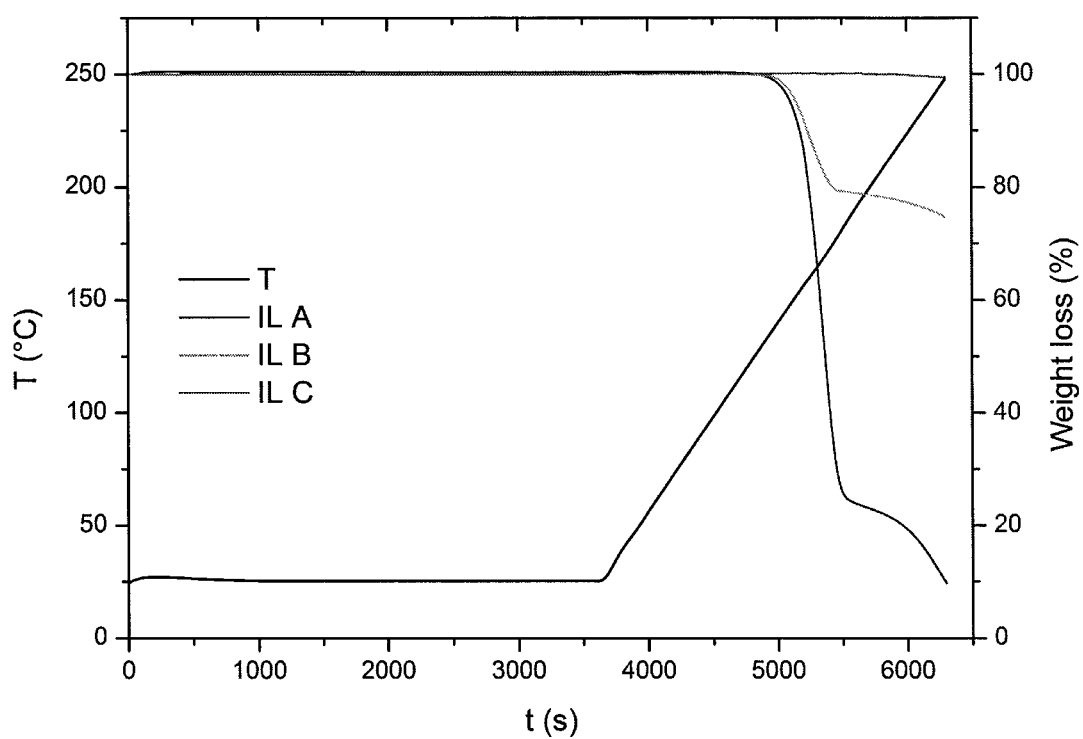
FIG. 4 shows a thermogravimetric analysis of IL A, B and C. The weight loss (volatility and/or decomposition) is measured in two steps, first at 25° C. for 1 h and subsequently the temperature is raised to 250° C. at 5° C./min. The carboxyl-based anions start to decompose at approx. 130° C.
Figure 5:
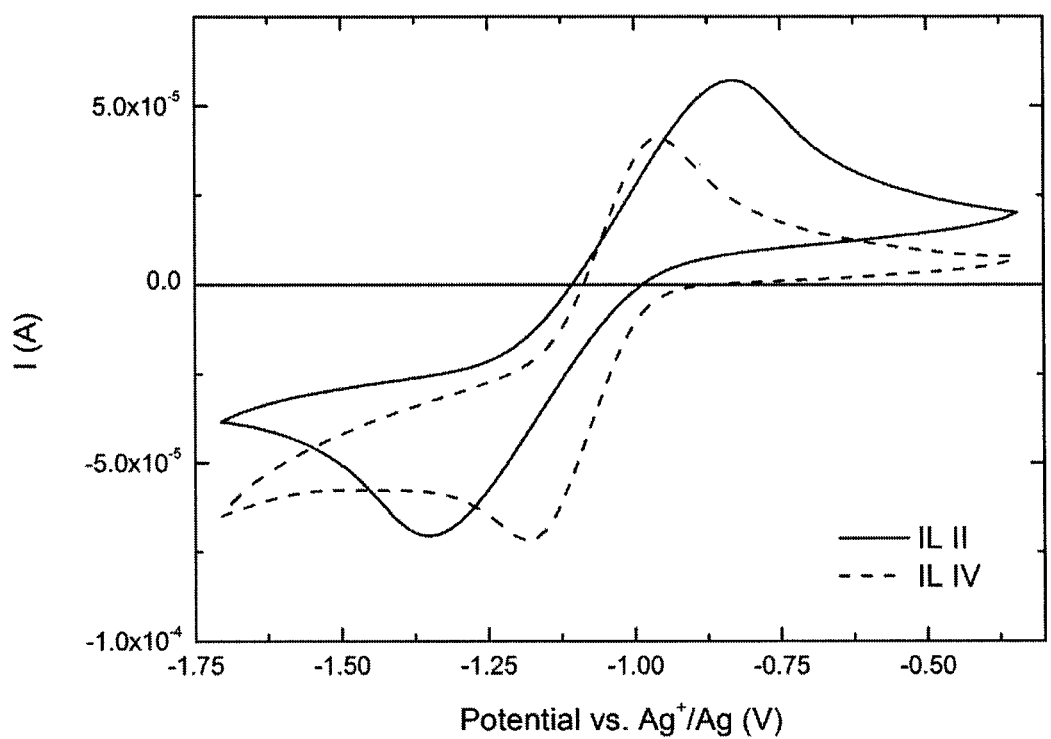
FIG. 5 shows cyclic voltammograms of IL II and IL IV saturated with oxygen gas at 25° C. A gold disk (φ=5.5 mm)
Figure 6:
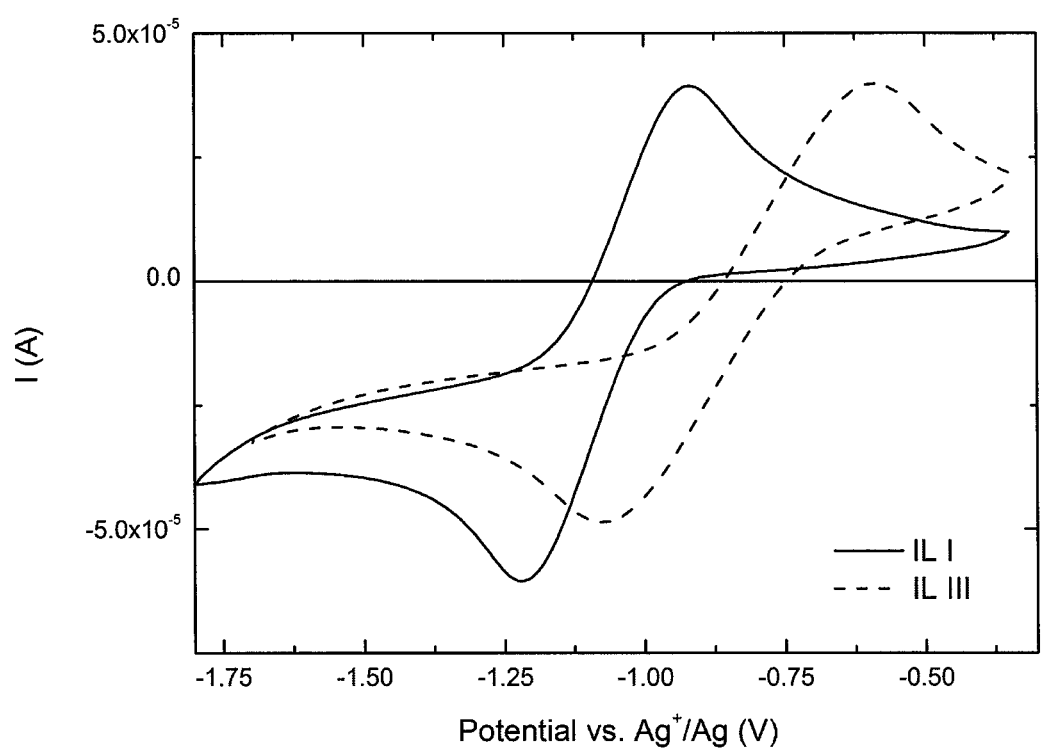

FIG. 6 shows analogous cyclic voltammograms of IL I and IL III saturated with oxygen gas at 25° C.

Figure 7:
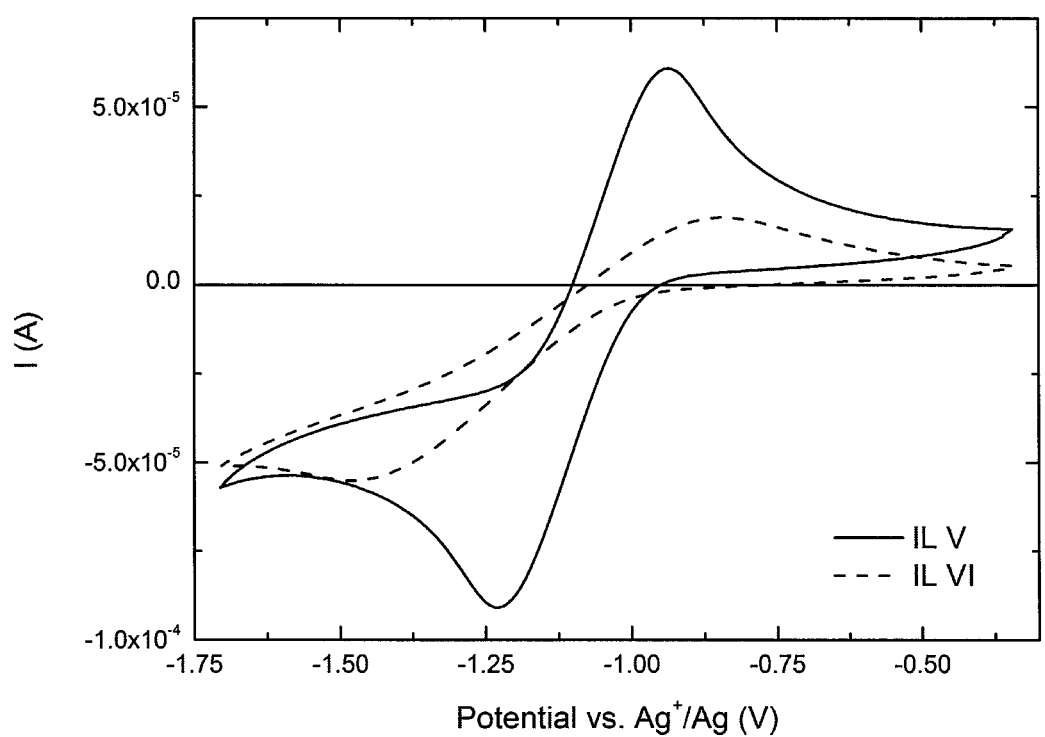

FIG. 7 shows analogous cyclic voltammograms of IL V and IL VI saturated with oxygen gas at 25° C.

Figure 8:
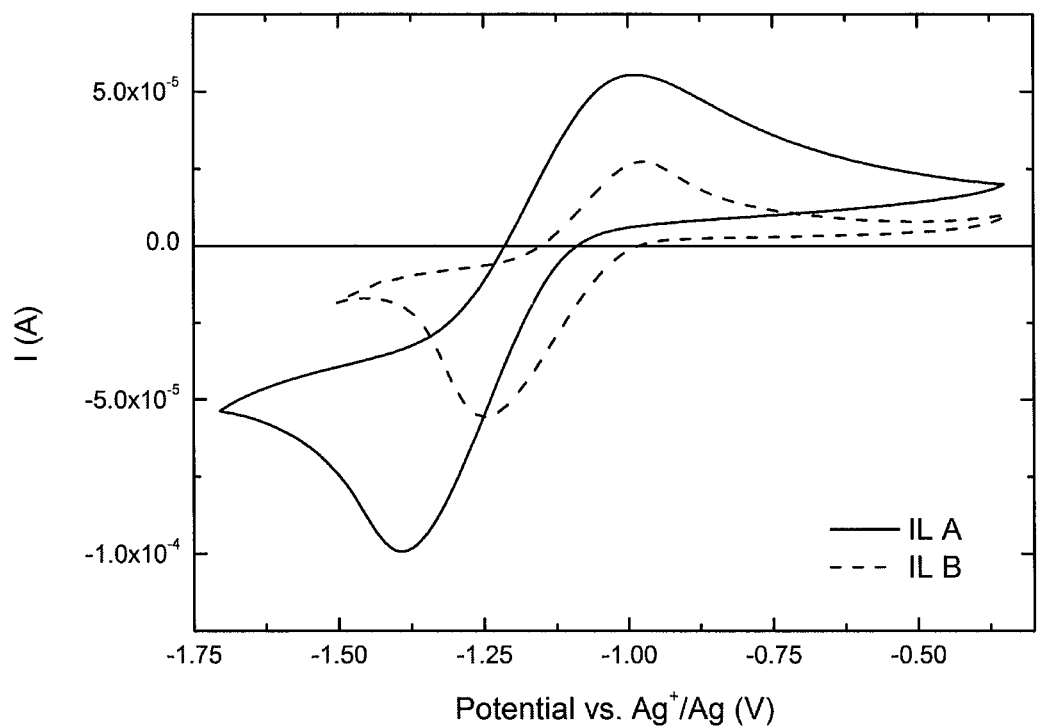

FIG. 8 shows cyclic voltammograms of IL A and IL B saturated with oxygen gas at 35° C. and 25° C., respectively. A gold disk (φ=5.5 mm) was used as working electrode and a platinum coil as counter electrode. A real reference electrode was a silver wire in a glass tube with an acetonitrile solution of 0.01 M silver nitrate and 0.1 M tetrabutylammonium perchlorate, separated from the electrolyte using a glass frit. The scan rate was 100 mV s$^{-1}$ and each third cycle is shown.

Figure 9:
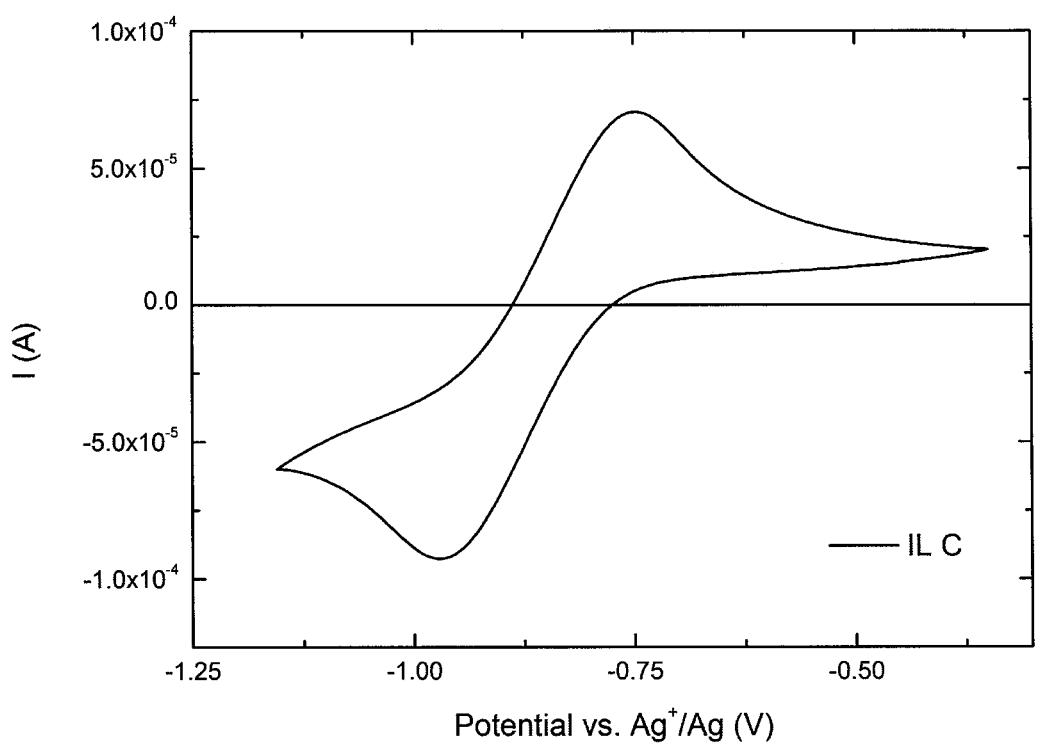

FIG. 9 shows a cyclic voltammogram of IL C saturated with oxygen gas at 25° C. A gold disk (φ=5.5 mm) was used as working electrode and a platinum coil as counter electrode. A real reference electrode was a silver wire in a glass tube with an acetonitrile solution of 0.01 M silver nitrate and 0.1 M tetrabutylammonium perchlorate, separated from the electrolyte using a glass frit. The scan rate was 100 mV s$^{-1}$ and each third cycle is shown.

DETAILED DESCRIPTION OF THE INVENTION

The ionic compounds of the present invention are also described as "ionic liquids" and the cation-anion combinations are in most cases liquids at room temperature. In some cases, a liquid state is achieved at temperatures slightly above room temperature. In the present invention, "ionic liquid" (IL) is understood to be a cation-anion combination with a melting point of at most 100° C. For practical applications in automotive batteries, room temperature ionic liquids are preferred (or species that are liquid at temperatures slightly above room temperature).

In the present invention, an ether function is incorporated in cationic compounds of formula (1). It is believed that the ether oxygen atom (O) is important to provide stability against $O_2^-$ radicals, and that the ether oxygen atom improves battery performance.

In order to synthesize cationic compounds of formula (1), generally appropriate procedures may appropriately include the following three steps: (1) synthesis of fluorinated precursor, (2) formation of an ionic liquid with halide anion (=quaternization), and (3) exchange of halide anion with bistriflimide (metathesis reaction).

Concerning step (1) in the above generally appropriate reaction scheme, the synthesis of fluorinated precursor, in particular the synthesis of the corresponding fluorinated amine ether, may be based on a similar method to that used by Kim et al., "Low melting inorganic salts of alkyl-, fluoroalkyl-, alkyl ether-, and fluoroalkyl ether-substituted oxazolidine and morpholine", *Inorganic Chemistry* 43, no. 9 (2004): 2960-2966. The present inventors have however observed that instead of 1.25 equivalents NaH it is advisable to use 1.5-1.8 equivalents. For the workup, column chromatography with diethyl ether serving as an eluent (100% $Et_2O \rightarrow Et_2O$ with 5% volume % of MeOH) can be applied and the desired product comes as the last fraction. Either one longer column or two shorter columns can be used.

Concerning step (2) in the above generally appropriate reaction scheme, i.e. synthesis of the iodide salt, the fluorinated amine ether obtained in step (1) is appropriately dissolved in acetonitrile and cooled down in an icebath. Methyl iodide (1 eq.), as an example of an alkyl iodide, may be added in small portions to the solution. After addition, the reaction mixture is stirred for 3 hours or until the amine has reacted completely, as monitored via TLC. After this time, the solvent is evaporated to give pure iodide IL.

Concerning step (3) in the above generally appropriate reaction scheme, to make a final product with a new anion, such as $Tf_2N$, the iodide salt obtained in step (2) may be dissolved in 30 mL of water and mixed with a water solution of lithium bis(trifluoromethylsulfonyl)imide (1.5 eq) causing an immediate occurrence of an IL phase on the bottom of the flask. After stirring for 30 minutes, dichloromethane may be added, the organic phase separated and washed with 50 mL distilled water. When the $AgNO_3$ test performed on the last water portion from washing gives a negative result for iodide ions, the solvent is evaporated to yield a pure IL.

In step (1) above, the fluorinated amine ether may be prepared by combining a perfluorinated alcohol (without fluorine atoms on the OH group-bearing carbon atom) with a Cl—$CH_2$—$CH_2$—N-(heterocycle/alkyl) compound, where the latter may advantageously be a 2-chloroethyl-pyrrolidine derivative or 2-chloroethyl-piperidine derivative. 2-chloroethyl derivatives can more generally be used as appropriate precursors, and a number of commercial chloro precursors exist. For example, for the imidazolium based ionic liquids, 1-(2-chloroethyl)-2-methyl-1H-imidazole hydrochloride could be used, and for the pyridinium based ionic liquids, 2-(chloromethyl)pyridine hydrochloride. For the morpholinium based ionic liquids, 4-(2-chloroethyl) morpholine hydrochloride) could be used. A 2-chloroethyl trialkylamine can be used to prepare non-heterocyclic precursors.

In the present invention, the anion serving as counter ion for cationic compounds of formula (1) may advantageously be chosen from the group consisting of: $C_nF_{2n+1}$—$SO_2$—N—$SO_2$—$C_mF_{2m+1}^-$, $PF_6^-$, $BF_4^-$, $C_nF_{2n+1}COO^-$, $C_nF_{2n+1}SO_3^-$ where n and m lie between 1 and 10. Perfluorocarboxylate anions are described for example in Lueckmann, M., R. H. Schuster, V. Dehnke, and A. Rosenplaenter. "Effects of ionic liquids on fluorinated rubber." *KGK KAUTSCHUK GUMMI KUNSTSTOFFE* 65, no. 5 (2012): 26-32. Perfluorosulfonate anions are reported in: Forsyth, Stewart A., Kevin J. Fraser, Patrick C. Howlett, Douglas R. MacFarlane, and Maria Forsyth. "N-methyl-N-alkylpyrrolidinium nonafluoro-1-butanesulfonate salts: Ionic liquid properties and plastic crystal behavior." *Green Chemistry* 8, no. 3 (2006): 256-261.

In the framework of the present invention, the ionic compounds of the present invention can also be used in combination with ionic liquids also described elsewhere, such as [BMPyrr][$Tf_2N$], [BMPyrr][$PF_6$], [DEME][$Tf_2N$], [PP13][$PF_6$], [PP13][$Tf_2N$], [$P_{6,6,6,14}$][Cl], [$C_2$mim][$BF_4$], [$C_4$mim][$BF_4$]. The preceding is a non-exhaustive illustrative list of combinations of the more commonly used cations and anions for battery applications.

It is also possible to envisage using the fluorinated ILs of the present invention as additives in other electrolytes (ionic liquids or just solvents typically used in non-aqueous batteries such as DME, triglyme, tetraglyme, PC, DMSO, DMF etc.) in order to increase the $O_2$ solubility of the final electrolyte. An ionic liquid is inherently conductive, which is not the case for a fluorinated additive, like a polyfluorocarbon (PFC) neutral molecule. When using ionic liquids as an additive the risk of evaporation of the additive is avoided and thus also degradation of the performance of the additive.

To use the materials of the present inventions as electrolyte component in a metal-air battery, the ionic compounds/liquids are appropriately mixed together with a metal salt. An electrolyte for the metal air battery is thus appropriately one that contains:

a fluorinated ionic liquid of the present invention; and a metal salt, the metal being an alkali, an alkali earth metal or a lanthanide metal, preferentially Li, Na, Mg, Ca, most preferentially Li salts. Preferable examples of Li salts that may be used include LiFSI, LiTFSI, $LiClO_4$, $LiBF_4$, $LiPF_6$, LiTDI (lithium 4,5-dicyano-2-(trifluoromethyl)-1-ide), lithium (trifluoromethanesulfonyl)-(nonafluorobutanesulfonyl)imide (LiIM14) and lithium bis(pentafluoroethanesulfonyl)imide (LiBETI).

The fluorinated ionic liquids of the invention can in principle be used in any metal-air battery in combination with any cathode e.g. composed of carbon, CNT, graphene, precious metals such as gold, metals such as nickel, aluminum; the metal or precious metals being in form of a foil, a foam, or included as part of a composite electrode itself made of i) conductive materials (carbon, CNT, graphene, metal, precious metal . . . ) possibly mixed with ii) a binder (PTFE, PvDF, Nafion, Lithiated-nafion . . . ) and/or possibly mixed with iii) a solid state catalyst (Mo, $MoO_3$, $MnO_2$, $Co_3O_4$, $MoS_2$, Au . . . ) facilitating the decomposition of the discharge product during the charge of the battery or anode materials (Li . . . ).

Metal-air batteries of the present invention include Li-air, Na-air, Mg-air, Zn-air, Sn-air and Si-air batteries. In a metal-air battery of the present invention, such as a lithium-air battery, the negative electrode (which may also be referred to as "anode" hereinafter) comprises at least an anode active material (which may also be referred to as "negative electrode active material" hereinafter). As the anode active material, general anode active materials for metal batteries such as lithium batteries can be used and the anode active material is not particularly limited. In general, the anode active material is able to store/release a metal ion ($Li^{+}$ $Na^{+}$ $K^{+}$ . . . ), $Li^+$ ions being present in Li-air batteries, $Na^+$ ions in Na-air batteries etc. Specific anode active materials are, for example, metals such as Li, Na, Mg, K, Al, Ca, Zn, Fe, Sn, Si, alloys, oxides and nitrides of the metals, and carbonaceous materials.

Specific anode active materials for rechargeable lithium-air batteries are, for example, a lithium metal, lithium protected anodes, lithium alloys such as a lithium-aluminium alloy, a lithium-tin alloy, a lithium-lead alloy and a lithium-silicon alloy, metal oxides such as a tin oxide, a silicon oxide, a lithium-titanium oxide, a niobium oxide and a tungsten oxide, metal sulfides such as a tin sulfide and titanium sulfide, metal nitrides such as a lithium-cobalt nitride, a lithium-iron nitride and a lithium manganese nitride, and carbonaceous materials such as graphite. Of these, lithium metal is preferred.

In a "lithium-protected anode"/"lithium Protected Electrode" (LPE), usually the Li is covered by a solid electrolyte (for example LISICON with formulae $LiM_2(PO_4)_3$). Between the LiSiCON and the Li metal, there is usually an interlayer (for example consisting of $Cu_3N/Li_3N$). In LPE systems, Li metal can be attached directly to one side of LiSiCON material, or alternatively a small amount of solvent containing a Li salt electrolyte may be added between the LiSiCON material and the Li metal to ensure Li ionic conductivity. Such materials have been described in, for example, U.S. Pat. Nos. 7,282,295, 7,491,458. LiSiCON materials have also been described in Nature Materials, 10, 682-686 (2011).

When a metal, alloy or the like in the form of foil or metal is used as the anode active material, it can be used as the anode itself.

The anode is required to contain at least an anode active material; however, as needed, it can contain a binder for fixing the anode active material. The type and usage of the binder are the same as those of the air cathode described above.

In general, an anode collector is connected to the anode, which collects current from the anode. The material for the anode collector and the shape of the same are not particularly limited. Examples of the material for the anode collector include stainless steel, copper, nickel, carbon and the like. Examples of the form of the anode collector include a foil form, a plate form and a mesh (grid) form.

In the metal-air, e.g. lithium-air, battery of the present invention, the positive electrode uses oxygen as a positive-electrode active material. Oxygen serving as the positive-electrode active material may be contained in air or oxygen gas. Examples of oxygen supply source include the air and oxygen gas, and preferred is oxygen gas. The pressure of the supplied air or oxygen gas is not particularly limited and can be appropriately determined. It is possible for the battery of the present invention to be completely encased in an oxygen-permeable membrane, advantageously one which shows selectivity for oxygen diffusion over that of water or that of carbon dioxide ($CO_2$).

In the metal-air e.g. lithium-air battery of the present invention, a separator may advantageously be provided between the air cathode and the anode for complete electrical insulation between these electrodes. The separator is not particularly limited as long as it is able to electrically insulate the air cathode and the anode from each other and has a structure that allows the electrolyte to be present between the air cathode and the anode.

Examples of the separator include porous films and non-woven fabrics comprising polyethylene, polypropylene, cellulose, polyvinylidene fluoride, glass ceramics, etc. Of these, a separator made of glass ceramics is preferred.

The metal-air battery of the present invention may appropriately be composed of one-compartment cell(s) or two-compartment cell(s). In the first case, typically one electrolyte is used between the anode and the air cathode together with a separator. In the second case, typically two different electrolytes are used at the anode side and cathode side called anolyte and catholyte, respectively; these two electrolytes are separated by a membrane able to conduct cations, such as $Li^+$ cation in particular. Ohara glass is one example of such a solid conductive membrane. In this later case, no separator is needed as the membrane acts as a kind of separator. In the case of a two-compartment cells, ionic compounds described in this invention will be preferably used as a catholyte, i.e. at the air cathode side.

The shape of the metal-air battery of the present invention is not particularly limited. Examples thereof include coin shapes, button shapes, sheet shapes, rectangular/prismatic shapes and laminate shapes. The lithium-air battery may have large shapes for use in (plug-in) hybrid or electric vehicles (cars . . . ) and the like.

The metal-air battery of the present invention may be used as a primary battery or a rechargeable secondary battery.

The metal-air battery thus prepared using fluorinated ionic liquids of the present invention can be used in any devices (computers, phones . . . ) or in automotive applications or stationary applications. It can be assembled in battery packs.

Within the practice of the present invention, it may be envisaged to combine any features or embodiments which have hereinabove been separately set out and indicated to be advantageous, preferable, appropriate or otherwise generally applicable in the practice of the invention. The present description should be considered to include all such combinations of features or embodiments described herein unless such combinations are said herein to be mutually exclusive or are clearly understood in context to be mutually exclusive.

EXPERIMENTAL SECTION—EXAMPLES

The following experimental section illustrates experimentally the practice of the present invention, but the scope of the invention is not to be considered to be limited to the specific examples that follow.

Analysis Methods: Determination of Dissolved Oxygen Concentration, Viscosity and Thermal Stability All ionic liquids were dried on a vacuum line at 70° C. for 72 hours and subsequently stored in an argon filled glove box with oxygen and water concentrations below 1 ppm. The water concentration in the ionic liquid was measured by Karl Fischer Coulometry and was always below 20 ppm.

Viscosity (dynamic and kinematic) and density of the ionic liquid was measured by an Anton Paar DMA 4500 M meter at 25.00° C.

Thermogravimetric analysis was performed by using a SDT Q600 (T.A. Instruments) under a constant argon flow. First the mass was monitored for 60 min at 25.00° C. to evaluate the volatility at room temperature. Subsequently the temperature was increased to 250.00° C. at 5° C./min, to evaluate the volatility and thermal stability at higher temperatures.

All electrochemical experiments were performed using a three electrode set up. This cell was filled and closed inside the glove box, followed by gas bubbling outside the glove box. Oxygen gas (≥99.9995%, Air Liquid, ALPHAGAZ 2) was used for the dissolution of oxygen in the ionic liquid. The gas was bubbled through the ionic liquid via a glass tube with a P2 glass filter for 30 minutes. The bubbler was connected to the gas bottle using silicon tubing. To avoid water contamination during bubbling, an extra drying tower (Sigma-Aldrich) was used, filled with activated molecular sieves 3 Å (beads, 4-8 mesh, Sigma-Aldrich) and placed between the gas bottle and the electrochemical cell. The molecular sieves were activated overnight at a temperature of 250° C. under a flow of argon. All glassware used for the experiments was dried overnight in an oven at 120° C. and transferred into the glove box while hot. All electrochemical measurements were performed using an Autolab 302N bipotentiostat controlled with NOVA 1.11.1 software. Two different working electrodes were used, (1) a gold disk macro electrode (φ=5.5 mm, Pine Instrumentations) or (2) a gold ultramicro electrode (φ=25 μm, CH Instruments Inc.) The real reference electrode was a silver wire (≥99.98%, Chempur) in a glass tube filled with an acetonitrile solution of 0.01 M silver nitrate and 0.1 M tetrabutylammonium perchlorate, which was separated from the electrolyte by a glass frit. The reference tube was assembled at least 30 minutes prior to the electrochemical measurement. A platinum coil was used as counter electrode. The electrochemical cell was placed in an oil bath at 25.0±0.2° C.

The dissolved oxygen concentration was calculated by combining the Cottrell equation (Eq. 1) on a macro electrode and the steady-state current on an ultramicro electrode described by Eq. 2 for the reduction of oxygen $$O_2 + e^- \rightarrow O_2^-:$$

$$i(t) = \frac{nFAD^{1/2}C}{\pi^{1/2}t^{1/2}} \tag{1}$$

$$i_{ss} = 4nFCDr \tag{2}$$

Both current profiles were recorded via a potentiostatic measurement at a potential where the oxygen reduction reaction is limited by mass-transfer and thus under diffusion control. All new ionic liquids were measured and compared to two commercial ionic liquids 1-butyl-1-methylpyrrolidinium bis(trifluoromethylsulfonyl)imide [BMPyrr][Tf$_2$N] and N,N-diethyl-N-methyl-N-(2-methoxyethyl)ammonium bis(trifluoromethylsulfonyl)imide [DEME][Tf$_2$N]. For these commercial ionic liquids the dissolved oxygen concentration was measured using the same set-up and method as for the new ionic liquids (described above).

Example 1: Synthesis/Characterization of IL II

Precursor: N-((2,2,3,3,4,4,5,5-octafluoropentoxy)ethyl)pyrrolidine

The synthesis of the first precursor for each IL called with Roman numbers was based on the paper of Kim, Jinwi, Rajendra P. Singh, and Jeanne M. Shreeve. "Low melting inorganic salts of alkyl-, fluoroalkyl-, alkyl ether-, and fluoroalkyl ether-substituted oxazolidine and morpholine." *Inorganic Chemistry* 43, no. 9 (2004): 2960-2966.

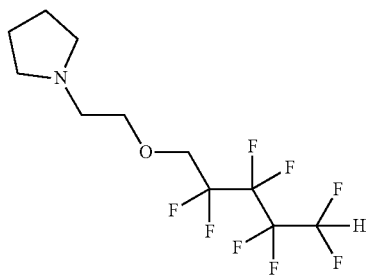 [SMILES: FC(F)C(F)(F)C(F)(F)C(F)(F)COCCN1CCCC1]

Sodium hydride (2.20 g, 91.9 mmol) in dry THF (60 mL) was cooled down to 0° C. 2,2,3,3,4,4,5,5-Octafluoro-1-pentanol (10.23 mL, 73.52 mmol) was added dropwise and the mixture was stirred at room temperature for 1 h. Then, N-(2-Chloroethyl)pyrrolidine hydrochloride (12.50 g, 73.52 mmol) was added and the mixture was stirred for additional 1 h at RT. Afterwards, the mixture was refluxed at 70° C. for 2 h and at 65° C. for 22 h. After this time, water was added to the mixture and the product was extracted with DCM and the DCM phase was dried with MgSO$_4$. The residue was purified on a silica gel column in EtOAc. A second column chromatography was needed to purify the product in 7:3, heptane:EtOAc, to give 5.24 g of yellow oil (21%).

$^1$H NMR (300 MHz, CDCl$_3$): δ=6.12 (tt, 1H), 3.98 (t, 2H), 3.74 (t, 2H), 2.71 (t, 2H), 2.55 (m, 4H), 1.78 (m, 4H) ppm $^{13}$C NMR (75 MHz, CDCl$_3$): δ=118.1 (m), 115.3 (m), 113.0 (m), 110.9 (m), 110.2 (m), 107.7 (m), 105.2 (m), 72.2 (s), 67.7 (t), 55.3 (s), 54.6 (s), 23.5 (s) ppm Precursor: N-((2,2,3,3,4,4,5,5-octafluoropentoxy) ethyl)-N-methylpyrrolidinium Iodide

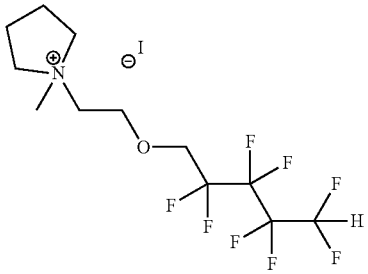 [SMILES: C[N+]1(CCOCC(F)(F)C(F)(F)C(F)(F)C(F)F)CCCC1 ; [I-]]

N-((2,2,3,3,4,4,5,5-octafluoropentoxy)ethyl)pyrrolidine (4.10 g, 12.4 mmol) was dissolved in 150 mL acetonitrile and cooled down in an icebath. Methyl iodide (0.98 mL, 12.4 mmol) was added in small portions to the solution. After addition the reaction mixture was stirred for 3 h or until N-((2,2,3,3,4,4,5,5-octafluoropentoxy)ethyl)pyrrolidine reacted completely, as monitored via TLC. After this time, the solvent was evaporated to give 5.60 g (96%) of pure iodide IL.

$^1$H NMR (300 MHz, CDCl$_3$): δ=6.07 (tt, 1H), 4.23 (t, 2H), 4.13 (m, 4H), 3.88 (m, 4H), 3.35 (s, 3H), 2.32 (m, 4H) ppm The IL N-((2,2,3,3,4,4,5,5-octafluoropentoxy)ethyl)-N-methylpyrrolinium bis(trifluoromethanesulfonyl)amide

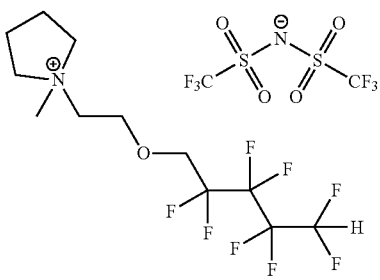 [SMILES: C[N+]1(CCOCC(F)(F)C(F)(F)C(F)(F)C(F)F)CCCC1 ; O=S(=O)([N-]S(=O)(=O)C(F)(F)F)C(F)(F)F]

N-((2,2,3,3,4,4,5,5-octafluoropentoxy)ethyl)-N-methylpyrrolidinium iodide (5.60 g, 11.9 mmol) was dissolved in 30 mL of ethanol and mixed with an ethanol solution of lithium bis(trifluoromethylsulfonyl)imide (3.75 g, 13.1 mmol). After stirring for 15 minutes, the solvent was evaporated, the residue dissolved in dichloromethane and washed in 3 portions with 80 mL distilled water. The AgNO$_3$ test performed on the last water portion from washing gave negative result for iodide ions. The solvent was evaporated to yield a brown liquid which was dried in vacuum at 70° C. overnight (m=6.98 g, yield: 94%).

$^1$H NMR (300 MHz, acetone-d$_6$): δ=6.73 (tt, 1H, J$_1$=51.0 Hz, J$_2$=5.3 Hz), 4.32 (br t, 2H), 4.30 (t, 2H, J=14.5 Hz), 3.93 (t, 2H, J=4.6 Hz), 3.83 (m, 4H), 3.36 (s, 3H), 2.35 (m, 4H), ppm $^{13}$C NMR (75 MHz, acetone-d$_6$): δ=121.1 (q), 116.6 (t), 111.9 (m), 109.2 (t), 106.6 (t), 68.2 (t), 67.5 (br), 66.3 (s), 64.2 (br), 49.6 (br), 22.2 (s) ppm $^{19}$F NMR (565 MHz, acetone-d$_6$): δ=−78.7 (s), −119.4 (m), −124.5 (m), −129.6 (m), −137.8 (d) ppm IR (ATR, cm$^{-1}$): 2970, 1349 (S=O), 1279, 1170 (S=O), 1132, 1054, 514 (C—F)

CHN, with catalyst, % (calculated): C: 26.93 (26.93), H: 4.20 (2.91), N: 4.35 (4.49).

MS-ESI (positive mode), found: m/z=344.3 (M$_{cation}$) and m/z=967.9 (2M$_{cation}$+M$_{anion}$).

Example 2: Synthesis/Characterization of IL IV

Precursor: N-((Trifluoroethoxy)ethyl)pyrrolidine

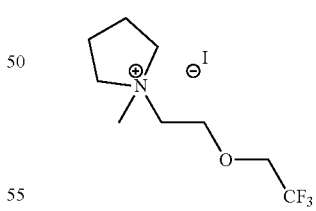

Sodium hydride, 60% suspension in mineral oil (4.34 g, 106 mmol) in dry THF (60 mL) was cooled down to 0° C. 2,2,2-Trifluoroethanol (4.30 mL, 59 mmol) was added dropwise and the mixture was stirred at room temperature for 1 h. Then, 1-(2-Chloroethyl)pyrrolidine hydrochloride (10.0 g, 59 mmol) was added and the mixture was stirred for additional 1 h at RT. Afterwards, the mixture was stirred at 70° C. for 18 h. After this time water was added to the mixture and the product was extracted with diethyl ether. After evaporation of the solvents, the crude product was re-dissolved in diethyl ether and purified on silica gel column. 2.59 g of yellow oil was obtained (Yield: 22%).

$^1$H NMR (300 MHz, CDCl$_3$): δ=3.86 (q, 2H, J=8.7 Hz), 3.76 (t, 2H, J=5.8 Hz), 2.57 (t, 2H, J=5.8 Hz), 2.57 (m, 4H), 1.79 (m, 4H) ppm Precursor: N-((Trifluoroethoxy)ethyl)-N-methyl Pyrrolidinium Iodide N-((Trifluoroethoxy)ethyl)pyrrolidine (5.18 g, 26.2 mmol) was dissolved in acetonitrile and cooled to 0° C. in an ice bath. Methyl iodide (1.63 mL, 26.2 mmol) was added in small portions. The resulting solution was stirred at room temperature for 3 h. Evaporation of the solvent yielded dark orange solid (quantitative yield). (m=7.74 g, 87%).

$^1$H NMR (300 MHz, D$_2$O): δ=4.11 (broad t, 2H), 4.04 (q, 2H, J=8.9 Hz), 3.64 (t, 2H, J=4.5 Hz), 3.56 (m, 4H), 3.08 (s, 3H), 2.20 (m, 4H) ppm

The IL: N-((Trifluoroethoxy)ethyl)-N-methyl Pyrrolidinium bis(tri-fluoromethanesulfonyl)amide

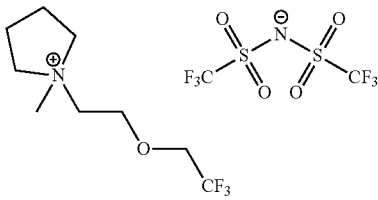

N-((Trifluoroethoxy)ethyl)-N-methyl pyrrolidinium iodide (7.74 g, 22.8 mmol) was dissolved in water and mixed with water solution of LiTf$_2$N (7.21 g, 25.1 mmol). After stirring for 15 min dichloromethane was added to the solution, the organic phase separated and washed with water until AgNO$_3$ test gave a negative result. Yield: 10.89 g, 97%.

$^1$H NMR (300 MHz, acetone-d): δ=4.32 (m, 2H), 4.20 (q, 2H, J=8.9 Hz), 3.94 (t, 2H, J=4.6 Hz), 3.84 (m, 4H), 3.37 (s, 3H), 2.36 (m, 4H) ppm $^{13}$C NMR (75 MHz, acetone-d$_6$): δ=125.0 (q), 121.0 (q), 68.5 (q), 67.1 (s), 66.3 (t), 64.1 (t), 49.5 (t), 22.2 (s) ppm $^{19}$F NMR (565 MHz, acetone-d$_6$): δ=−73.6 (t), −78.6 (s) ppm IR (ATR, cm$^{-1}$): 2981, 1348 (S═O), 1280, 1175 (S═O), 1131, 1052, 512 (C—F)

CHN, with catalyst, % (calculated): C: 26.81 (26.83), H: 4.71 (3.48), N: 4.56 (5.69).

MS-ESI (positive mode), found: m/z=212.2 (M$_{cation}$) and m/z=704.0 (2M$_{cation}$+M$_{anion}$).

Example 3: Synthesis/Characterization of IL I

Precursor of the IL: N-((Trifluoroethoxy)ethyl)piperidine

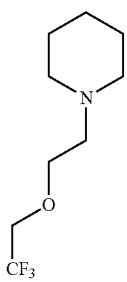

Sodium hydride (3.33 g, 139.0 mmol) in dry THF (60 mL) was cooled down to 0° C. 2,2,2-Trifluoroethanol (7.93 mL, 108.6 mmol) was added dropwise and the mixture was stirred at room temperature for 1 h. Then, 1-(2-Chloroethyl) piperidine hydrochloride (20.0 g, 108.6 mmol) was added and the mixture was stirred for additional 1 h at RT. Afterwards, the mixture was stirred at 78° C. for 11 h and at 65° C. for 23 h. After this time water was added to the mixture and the product was extracted with DCM, to give reddish oil. Dissolution of the oil in DCM and filtration yielded the unreacted piperidine substrate that was filtered off and oil that was purified on silica gel. Two subsequent column chromatography purifications were applied: one in pure DCM and one in 20% heptane/EtOAc to yield slightly yellow oil. The product has low vapour pressure, some product lost on solvent evaporation. (m=4.05 g, 12%).

$^1$H NMR (300 MHz, CDCl$_3$): δ=3.86 (q, 2H), 3.74 (q, 2H), 2.58 (t, 2H), 2.43 (t, 4H), 1.58 (m, 4H), 1.44 (m, 2H) ppm $^{13}$C NMR (75 MHz, chloroform-d): δ=119.9 (q), 70.5 (s), 68.5 (q), 58.4 (s), 54.9 (s), 25.9 (s), 24.2 (s) ppm Precursor of the IL: N-((Trifluoroethoxy)ethyl)-N-methylpiperidine

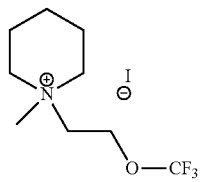

N-((Trifluoroethoxy)ethyl)piperidine (4.47 g, 22.7 mmol) was dissolved in 150 mL acetonitrile and cooled down in an icebath. Methyl iodide (1.41 mL, 22.7 mmol) was added in small portions to the solution. After addition the reaction mixture was stirred for 3 h or until N-((Trifluoroethoxy) ethyl)piperidine reacted completely, as monitored via TLC. After this time, the solvent was evaporated to give 7.66 g (96%) of pure iodide IL.

$^1$H NMR (300 MHz, D$_2$O): δ=4.13 (m, 2H), 4.06 (q, 2H, J=8.9 Hz), 3.64 (t, 2H, J=4.0 Hz), 3.41 (m, 4H), 3.12 (s, 3H), 1.89 (t, 4H, J=5.2 Hz), 1.65 (m, 2H) ppm

The IL: N-((Trifluoroethoxy)ethyl)-N-methylpiperidinium bis(tri-fluoromethanesulfonyl)amide

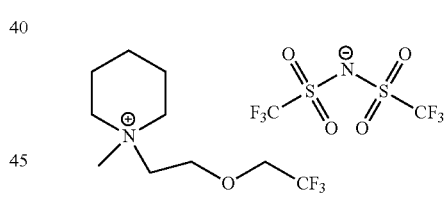

N-((Trifluoroethoxy)ethyl)-N-methylpiperidine (7.66 g, 21.7 mmol) was dissolved in 30 mL of water and mixed with a water solution of lithium bis(trifluoromethylsulfonyl)imide (6.85 g, 23.8 mmol) causing an immediate occurrence of an IL phase on the bottom of the flask. After stirring for 30 minutes, dichloromethane was added, the organic phase was separated and washed with 50 mL distilled water. The AgNO$_3$ test performed on the last water portion from washing gave negative result for iodide ions. The solvent was evaporated to yield an orange-brown liquid (m=10.0 g, 91%).

$^1$H NMR (300 MHz, CDCl$_3$): δ=4.12 (t, 2H, J=4.4 Hz), 3.93 (q, 2H, J=8.4 Hz), 3.70 (t, 2H, J=4.4 Hz), 3.45 (m, 4H), 3.16 (s, 3H), 1.95 (m, 4H), 1.75 (m, 2H) ppm $^{13}$C NMR (75 MHz, acetone-d$_6$): δ=123.5 (q), 119.7 (q), 68.4 (q), 65.5 (s), 63.1 (t), 62.81 (s), 50.0 (s), 20.6 (s), 20.0 (s) ppm $^{19}$F NMR (565 MHz, acetone-d$_6$): δ=−73.6 (t), −78.6 (s) ppm IR (ATR, cm$^{-1}$): 2955, 1348 (S=O), 1279, 1177 (S=O), 1133, 1053, 514 (C—F)

CHN, with catalyst, % (calculated): C: 28.51 (28.46), H: 5.07 (3.78), N: 5.42 (5.53).

MS-ESI (positive mode), found: m/z=226.2 ($M_{cation}$) and m/z=731.9 ($2M_{cation}+M_{anion}$).

Example 4: Synthesis/Characterization of IL III

Precursor: N-((2,2,3,3,4,4,5,5-octafluoropentoxy)ethyl)piperidine

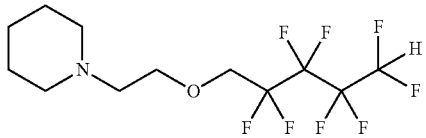 [SMILES: FC(F)C(F)(F)C(F)(F)C(F)(F)COCCN1CCCCC1]

Sodium hydride (4.0 g of 60% suspension, 100 mmol) in dry THF (60 mL) was cooled down to 0° C. 2,2,3,3,4,4,5,5-Octafluoro-1-pentanol (7.73 mL, 55.5 mmol) was added dropwise and the mixture was stirred at room temperature for 1 h. Then, N-(2-Chloroethyl)piperidine hydrochloride (10.23 g, 55.5 mmol) was added and the mixture was stirred for additional 1 h at RT. Afterwards, the mixture was refluxed at 78° C. for 3 h and at 65° C. overnight. After this time, water was added to the mixture and the product was extracted with Et$_2$O. The residue chromatographed on silica gel in diethyl ether. A second column chromatography was needed to purify the product (diethyl ether with increasing content of methanol).

$^1$H NMR (300 MHz, CDCl$_3$): δ=6.14 (tt, 1H, $J_1$=51.8 Hz, $J_2$=5.3 Hz), 3.98 (t, 2H, J=13.9 Hz), 3.73 (t, 2H, J=5.8 Hz), 2.56 (t, 2H, J=5.8 Hz), 2.42 (m, 4H), 1.58 (m, 4H), 2.50 (m, 2H) ppm $^{13}$C NMR (75 MHz, CDCl$_3$): δ=115.5 (m), 109.3 (m), 107.6, 105.9, 70.8 (s), 67.7 (t), 58.3 (s), 54.9 (s), 25.9 (s), 24.2 (s) ppm Precursor: N-((2,2,3,3,4,4,5,5-octafluoropentoxy)ethyl)-N-methylpiperidinium Iodide

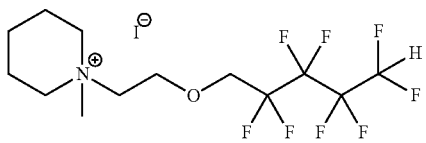 [SMILES: C[N+]1(CCOCC(F)(F)C(F)(F)C(F)(F)C(F)F)CCCCC1 ; [I-]]

N-((2,2,3,3,4,4,5,5-octafluoropentoxy)ethyl)piperidine (6.20 g, 18.0 mmol) was dissolved in 100 mL acetonitrile and cooled down in an icebath. Methyl iodide (1.12 mL, 18.0 mmol) was added in small portions. After addition the reaction mixture was stirred for 3 h. After this time, the solvent was evaporated to give a yellow solid in a quantitative yield.

$^1$H NMR (300 MHz, methanol-d$_4$): δ=6.59 (tt, 1H, $J_1$=51.2 Hz, $J_2$=5.7 Hz), 4.20 (t, 2H, J=13.6 Hz), 4.14 (br t, 2H), 3.73 (t, 2H, J=4.50 Hz), 3.48 (m, 4H), 3.18 (s, 3H), 1.95 (m, 4H), 1.73 (m, 2H) ppm The IL: N-((2,2,3,3,4,4,5,5-octafluoropentoxy)ethyl)-N-methylpiperidinium bis(trifluoromethanesulfonyl)amide

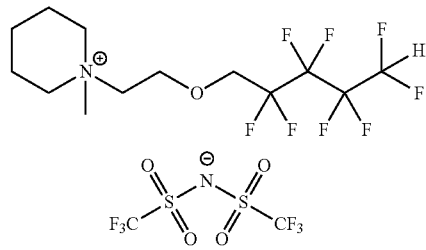 [SMILES: C[N+]1(CCOCC(F)(F)C(F)(F)C(F)(F)C(F)F)CCCCC1 ; O=S(=O)([N-]S(=O)(=O)C(F)(F)F)C(F)(F)F]

N-((2,2,3,3,4,4,5,5-octafluoropentoxy)ethyl)-N-methylpiperidinium iodide (8.78 g, 18.1 mmol) was dissolved in 50 mL of ethanol and mixed with an ethanol solution of lithium bis(trifluoromethylsulfonyl)imide (5.73 g, 19.9 mmol). After stirring for 15 minutes, the solvent was evaporated, the residue dissolved in dichloromethane and washed in 3 portions with 80 mL distilled water. The AgNO$_3$ test performed on the last water portion from washing gave negative result for iodide ions. The solvent was evaporated to yield a yellow liquid (9.94 g, 86%).

$^1$H NMR (300 MHz, methanol-d$_4$): δ=6.57 (tt, 1H, $J_1$=51 Hz, $J_2$=5.4 Hz), 4.18 (t, 2H, J=14.4 Hz), 4.23 (br t, 2H), 3.70 (t, 2H, J=4.3 Hz), 3.49 (m, 4H), 3.18 (s, 3H), 1.95 (m, 4H), 1.73 (m, 2H) ppm $^{19}$F NMR (565 MHz, methanol-d$_4$): δ=−79.4 (s, 6F), −119.9 (m, 2F), −125.1 (m, 2F), −130.3 (m, 2F), −138.5 (d, 2F) ppm IR (ATR, cm$^{-1}$): 2980, 1349 (S=O), 1280, 1175 (S=O), 1131, 1052, 511 (C—F)

CHN, with catalyst, % (calculated): C: 26.93 (28.49), H: 4.05 (3.16), N: 4.35 (4.39).

MS-ESI (positive mode), found: m/z=358.5 ($M_{cation}$) and m/z=996.0 ($2M_{cation}+M_{anion}$).

Example 5: Synthesis/Characterization of IL V

Precursor: N,N-diethyl-N-((Trifluoroethoxy)ethyl)amine

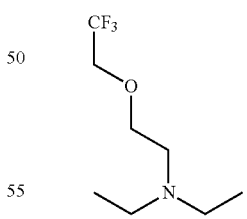

Sodium hydride (60% in mineral oil, 3.22 g, 80.5 mmol) in dry THF (25 mL) was cooled down to 0° C. 2,2,2-trifluoroethanol (4.70 mL, 64.4 mmol) was added dropwise and the mixture was stirred at room temperature for 1 h. Then, (2-chloroethyl)-N,N-diethylammonium hydrochloride (11.08 g, 64.4 mmol) was added and the mixture was stirred for additional 1 h at RT. Afterwards, the mixture was stirred at 78° C. for 3 h and at 70° C. for 17 h. After this time water was added to the mixture and the product was extracted with diethyl ether, to give a light yellow oil. A column chromatography (100% Et$_2$O) gave an impure product as the last fraction. A subsequent column chromatography (2% EtOH/DCM) was applied to yield the product as a transparent oil. The product has low vapour pressure, some product lost on solvent evaporation. (m=4.05 g, 12%).

$^1$H NMR (300 MHz, CDCl$_3$): δ=3.86 (q, 2H, J=8.6 Hz), 3.70 (t, 2H, J=5.5 Hz), 2.69 (t, 2H, J=5.8 Hz), 2.59 (q, 4H, J=6.7 Hz), 1.04 (t, 6H, J=6.7 Hz) ppm Precursor: N, N-diethyl-N-methyl-N-((Trifluoroethoxy)ethyl)ammonium Iodide

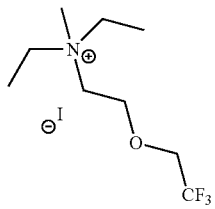

A solution of N, N-diethyl-N-((Trifluoroethoxy)ethyl) amine (0.63 g, 3.16 mmol) in ethanol remaining from the column and acetonitrile was cooled down in an ice bath. Then methyl iodide (0.12 mL, 3.16 mmol) was added dropwise. After the addition the ice bath was removed and the solution was stirred at ambient temperature for 3 h. Evaporation of the solvent gave the product, a yellow oil in a quantitative yield.

$^1$H NMR (300 MHz, CDCl$_3$): δ=4.27 (t, 2H, J=4.4 Hz), 4.05 (q, 2H, J=8.5 Hz), 3.97 (t, 2H, J=4.4 Hz), 3.67 (q, 4H, J=7.2 Hz), 3.34 (s, 21H), 1.43 (t, 6H, J=7.2 Hz) ppm IL: N, N-diethyl-N-methyl-N-((Trifluoroethoxy)ethyl)ammonium bis(trifluoromethanesulfonyl)amide

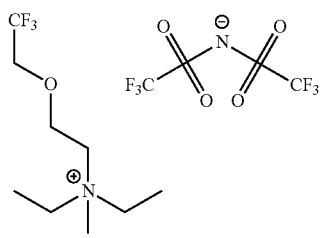

N, N-diethyl-V-methyl-N-((Trifluoroethoxy)ethyl)ammonium iodide (1.08 g, 3.17 mmol) and LiTf$_2$N (1.0 g, 3.48 mmol) were dissolved together in water and stirred for 10 min at ambient temperature. After this time dichloromethane (50 mL) was added and the resulting two-phase mixture was stirred vigorously for 10 min. After this time, mixture was taken up in a separation funnel, the DCM phase was separated and the water phase was washed once with DCM. The combined DCM phases were then washed with water until the AgNO$_3$ test gave a negative result for iodides. Evaporation of the mixture yielded the pure product, a yellow liquid (m=1.32 g, 83%).

$^1$H NMR (300 MHz, acetone-d$_6$): δ=4.29 (m, 2H), 4.18 (q, 2H, J=8.9 Hz), 3.84 (t, 2H, J=4.7 Hz), 3.68 (q, 4H, J=7.3 Hz), 3.29 (s, 3H), 1.43 (t, 6H, J=7.3 Hz) ppm $^{13}$C NMR (75 MHz, acetone-d$_6$): δ=123.9 (q), 120.2 (q), 67.7 (q), 65.4 (s), 59.9 (t), 57.5 (s), 47.7 (t), 7.27 (s) ppm $^{19}$F NMR (565 MHz, acetone-d$_6$): δ=−75.0 (t), −80.0 (s) ppm IR (ATR, cm$^{-1}$): 2958, 1348 (S=O), 1280, 1176 (S=O), 1132, 1052, 512 (C—F)

Example 6: Synthesis/Characterization of IL VI

Precursor: N, N-diethyl-N-((2,2,3,3,4,4,5,5-octafluoropentoxy)ethyl)amine

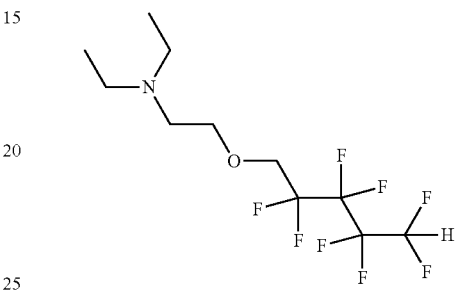

Sodium hydride, 60% suspension in mineral oil (2.20 g, 55.0 mmol) in dry THF (60 mL) was cooled down to 0° C. 2,2,3,3,4,4,5,5-octafluoro-1-pentanol (5.67 mL, 40.8 mmol) was added dropwise and the mixture was stirred at room temperature for 1 h. Then, (2-chloroethyl)-N,N-diethylammonium hydrochloride (8.12 g, 40.8 mmol) was added and the mixture was stirred for additional 1 h at RT and at 73° C. for 16 h. After this time water was added to the mixture and the product was extracted with diethyl ether. After evaporation of the solvent, the crude product was re-dissolved in diethyl ether and purified on two subsequent silica gel columns in this solvent. 2.70 g of yellow oil was obtained (Yield: 20%).

$^1$H NMR (300 MHz, CDCl$_3$): δ=6.11 (tt, 1H, J$_1$=51.7 Hz, J$_2$=5.6 Hz), 3.97 (t, 2H, J=13.9 Hz), 3.68 (t, 2H, J=5.8 Hz), 2.67 (t, 2H, J=5.9 Hz), 2.56 (q, 2H, J=6.9 Hz), 1.02 (t, 6H, J=6.9 Hz) ppm $^{13}$C NMR (75 MHz, chloroform-d): δ=115.5 (m), 111.0 (m), 107.7 (t), 105.2 (t), 71.7 (s), 67.8 (t), 52.3 (s), 47.6 (s), 11.7 (s) ppm Precursor: N, N-diethyl-N-methyl-N-((2,2,3,3,4,4,5,5-octafluoropentoxy)ethyl)ammonium Iodide

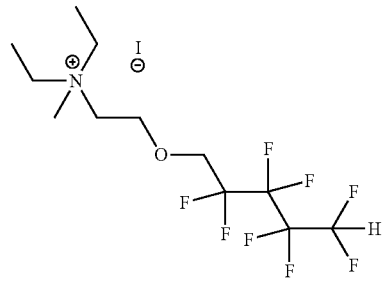 [SMILES: CC[N+](C)(CC)CCOCC(F)(F)C(F)(F)C(F)(F)C(F)F ; [I-]]

N,N-diethyl-N-((2,2,3,3,4,4,5,5-octafluoropentoxy)ethyl)amine (2.70 g, 8.15 mmol) was dissolved in acetonitrile and cooled down in an ice bath. Methyl iodide (0.51 mL, 8.15 mmol) was added in small portions to the solution. After addition the reaction mixture was stirred for 3 h or until the substrates have reacted completely, as monitored via TLC. Then, the solvent was evaporated to give 3.85 g (99%) of pure iodide IL.

$^1$H NMR (300 MHz, D$_2$O): δ=6.43 (tt, 1H, J$_1$=51 Hz, J$_2$=5.8 Hz), 4.13 (t, 2H, J=14.3 Hz), 4.02 (br, 2H), 3.50 (t, 2H, J=3.8 Hz), 3.35 (q, 4H, J=7.1 Hz), 2.95 (s, 3H), 1.25 (t, 6H, J=7.1 Hz) ppm IL: N, N-diethyl-N-methyl-N-((2,2,3,3,4,4,5,5-octafluoropentoxy)ethyl)ammonium bis(trifluoromethanesulfonyl)amide

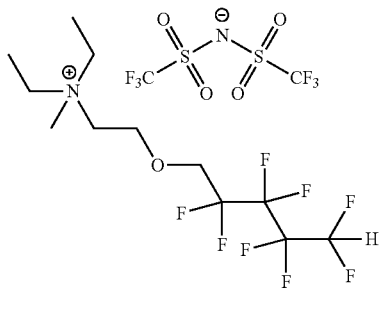 [SMILES: CC[N+](C)(CC)CCOCC(F)(F)C(F)(F)C(F)(F)C(F)F ; O=S(=O)([N-]S(=O)(=O)C(F)(F)F)C(F)(F)F]

N,N-diethyl-N-methyl-N-((2,2,3,3,4,4,5,5-octafluoropentoxy)ethyl)ammonium iodide (3.85 g, 8.14 mmol) was dissolved in 30 mL of ethanol and mixed with an ethanol solution of lithium bis(trifluoromethylsulfonyl)imide (2.56 g, 8.95 mmol). After stirring for 15 minutes, the solvent was evaporated, the residue dissolved in dichloromethane and washed in 3 portions with 80 mL distilled water. The AgNO$_3$ test performed on the last water portion from washing gave negative result for iodide ions. The solvent was evaporated to yield a yellow liquid (4.45 g, 87%).

$^1$H NMR (300 MHz, acetone-d$_6$): δ=6.74 (tt, 1H, J$_1$=51 Hz, J$_2$=5.5 Hz), 4.31 (t, 2H, br), 4.29 (t, 2H, J=14.4 Hz), 3.86 (t, 2H, J=4.3 Hz), 3.68 (q, 4H, J=7.3 Hz), 3.30 (s, 3H), 1.46 (t, 6H, J=7.3 Hz) ppm $^{13}$C NMR (75 MHz, acetone-d$_6$): δ=121.3 (q), 109.2 (t), 105.6 (t), 68.1 (t), 66.6 (s), 60.8 (t), 58.4 (t), 48.6 (t), 8.2 (s) ppm $^{19}$F NMR (565 MHz, acetone-d$_6$): δ=−78.6 (s, 6F), −119.4 (m, 2F), −124.5 (m, 2F), −129.6 (br, 2F), −137.8 (d, 2F) ppm IR (ATR, cm$^{-1}$): 2925, 1349 (S=O), 1170 (S=O), 1131, 1053, 513 (C—F)

Example 7: Synthesis/Characterization of IL A

N,N-butylmethylpyrrolidinium heptadecafluorobutanoate, BMPyrr C$_3$F$_7$COO

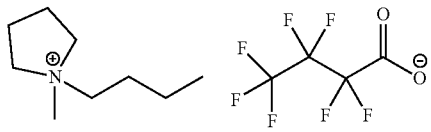

Aqueous saturated solution of potassium hydroxide was added dropwise to hexafluorobutanoic acid (15 g, 72 mmol) under stirring, until the pH slightly exceeded pH 7. To the resulting aqueous solution of potassium heptadecafluorobutanoate, 1-butyl-3-methylpyrrolidinium bromide was added (15.98 g, 72 mmol) and the solution was stirred for 30 min. No phase separation was observed. The water was carefully evaporated. Dichloromethane (100 mL) was added to the dry residue and the solution was placed in the fridge for 1 h to precipitate KBr. Filtration on the glass filter (porosity 4) and evaporation of DCM yielded a transparent oil which tested negative for bromides with AgNO$_3$.

$^1$H NMR (300 MHz, CDCl$_3$): δ=3.72 (m, 4H), 3.52 (m, 2H), 3.21 (s, 3H), 2.78 (m, 4H), 1.76 (m, 2H), 1.43 (m, 2H), 0.99 (t, 3H) ppm $^{19}$F NMR (565 MHz, CDCl$_3$): δ=−84.7 (t, 3F), −121.0 (q, 2F), −130.6 (broad s, 2F) ppm IR (ATR, cm$^{-1}$): 2968, 1686 (C=O), 1202 (C—O), 1110 (C—N), 528 (C—F)

Example 8: Synthesis/Characterization of IL B

N,N-butylmethylpyrrolidinium heptadecafluorononanoate, BMPyrr C$_8$F$_{17}$COO

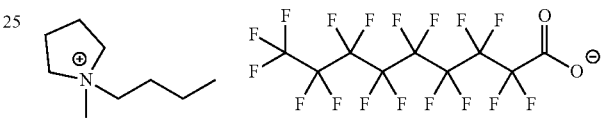

Potassium heptadecafluorononanoate (10.0 g, 19.9 mmol) was dissolved in 100 mL of a 1:1 solution of ethanol and acetone. BMPyrr Cl (3.36 g, 18.92 mmol) in 20 mL DCM was added and the mixture was stirred at room temperature for 20 min. After this time, the formed KCl precipitate was filtered off on a glass filter and the solvents were evaporated. The residue was re-dissolved in dry DCM and filtrated. Evaporation gave a slightly green transparent solid (m=11.43 g, 99.8%).

$^1$H NMR (300 MHz, CDCl$_3$): δ=3.72 (m, 4H), 3.51 (m, 2H), 3.20 (s, 3H), 2.26 (m, 4H), 1.74 (m, 2H), 1.43 (m, 2H), 0.98 (t, 3H) ppm $^{13}$C NMR (75 MHz, CDCl$_3$): cation peaks: δ=64.4 (s), 64.2 (s), 48.4 (s), 25.8 (s), 21.6 (s), 19.6 (s), 13.4 (s) ppm $^{19}$F NMR (565 MHz, CDCl$_3$): δ=−78.3 (t, 3F), −80.8 (m), −117.1 (m), −126.8 (broad s, 2F) ppm IR (ATR, cm$^{-1}$): 2976, 1679 (C=O), 1198 (C—O), 1147 (C—N), 527 (C—F)

CHN, % (calculated): C: 34.88 (35.71), H: 3.76 (3.33), N: 2.30 (2.31).

Example 9: Synthesis/Characterization of IL C

N,N-butylmethylpyrrolidinium nonafluorobutanesulfonate, BMPyrr C$_4$F$_9$SO$_3$

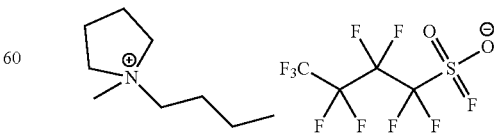

To BMPyrr Cl (18 g, 58.8 mmol), dissolved in 250 mL dichloromethane, lithium nonaflate (10.24 g, 57.7 mmol) was added and the suspension was stirred at room temperature for 1 h. After this time the solid residue (LiCl) was filtered off and the solvent evaporated. The solid was then re-dissolved in dry DCM and the precipitated remaining of LiCl was filtered off. AgNO$_3$ test was negative for halides. The solvent was evaporated and the IL was dried in vacuum to give 22.41 g (88%) of the product.

$^1$H NMR (300 MHz, CDCl$_3$): δ=6.07 (tt, 1H), 4.23 (t, 2H), 4.13 (m, 4H), 3.88 (m, 4H), 3.35 (s, 3H), 2.32 (m, 4H) ppm $^{13}$C NMR (75 MHz, CDCl$_3$): δ=122-103 ppm (overlapped multiplets), 64.4 (s), 64.2 (s), 48.4 (s), 25.8 (s), 21.6 (s), 19.6 (s), 13.4 (s) ppm $^{19}$F NMR (565 MHz, CDCl$_3$): δ=−79.6 (t, 3F), −113.5 (m, 2F), −120.4 (m, 2F), −124.7 (t, 2F) ppm IR (ATR, cm$^{-1}$): 2975, 1473, 1353 (S=O), 1253 (C—N), 1210 (S=O), 1132, 1050, 523 (C—F)

CHN, with catalyst, % (calculated): C: 35.33 (35.38), H: 4.20 (4.57), N: 3.36 (3.17).

Results

In Table 1 below, fluorinated cations based on ether functionalized piperidinium cations (IL I, IL III); based on ether functionalized pyrrolidinium cations (IL II, IL IV) and based on ether functionalized quaternary ammonium (IL V, IL VI) were tested. The [DEME][Tf$_2$N] and [BMPyrr][Tf$_2$N] are commercial samples as comparison. The O$_2$ concentration, and viscosity (dynamic and kinematic) were measured with the same experimental set up. In these tests, cations according to the invention were combined with TFSI$^-$ anions.

TABLE 1

| Ionic Liquid | Structure of Ionic Liquids | $C_{O2}$ (mol m$^{-3}$) | Dynamic viscosity (mPa s) | Kinematic viscosity (mm$^2$ s$^{-1}$) |
|---|---|---|---|---|
| [BMPyrr][Tf$_2$N] | Commercial sample for reference | 4.5 ± 0.2 | 82.8 ± 0.2 | 59.4 ± 0.2 |
| IL II | | 7.6 ± 0.2 | 320 ± 2 | 199 ± 1 |
| IL IV | | 29.9 ± 0.6 | 115 ± 1 | 75.5 ± 0.7 |
| IL I | | 12.0 ± 0.4 | 228.0 ± 0.4 | 151.5 ± 0.3 |
| IL III | | 15.6 ± 0.3 | 587 ± 5 | 371 ± 3 |

TABLE 1-continued

| Ionic Liquid | Structure of Ionic Liquids | $C_{O2}$ (mol m$^{-3}$) | Dynamic viscosity (mPa s) | Kinematic viscosity (mm$^2$ s$^{-1}$) |
| --- | --- | --- | --- | --- |
| [DEME][Tf$_2$N] | Commercial sample for reference | 5.1 ± 0.1 | 76.8 ± 0.3 | 54.6 ± 0.2 |
| IL V | | 26.7 ± 0.6 | 143.7 ± 0.2 | 97.0 ± 0.2 |
| IL VI | | 40.3 ± 0.8 | 446 ± 4 | 85 ± 2 |

In Table 2 below, fluorinated anions based on a carboxyl or sulfonate functional groups were studied. For Ionic Liquid A, the measurements were done at 35° C. since this Ionic Liquid is not a Room Temperature Ionic Liquid.

TABLE 2

| Ionic Liquid | Structure | $C_{O2}$ (mol m$^{-3}$) | Dynamic viscosity (mPa s) | Kinematic viscosity (mm$^2$ s$^{-1}$) |
| --- | --- | --- | --- | --- |
| [BMPyrr][Tf$_2$N] | Commercial sample for reference | 4.5 ± 0.2 | 82.8 ± 0.2 | 59.4 ± 0.2 |
| A | 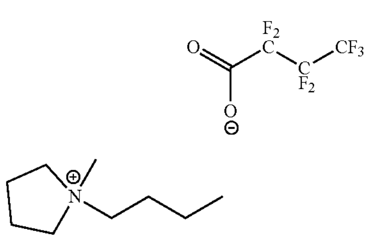 | 6.7 ± 0.1 (at 35° C.) | 178 ± 2 (at 35° C.) | 138 ± 1 (at 35° C.) |

TABLE 2-continued

| Ionic Liquid | Structure | $C_{O2}$ (mol m$^{-3}$) | Dynamic viscosity (mPa s) | Kinematic viscosity (mm$^2$ s$^{-1}$) |
|---|---|---|---|---|
| B | 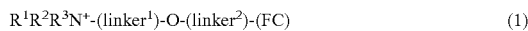 | 29.4 ± 0.6 | 185 ± 4 | 128 ± 3 |
| C | 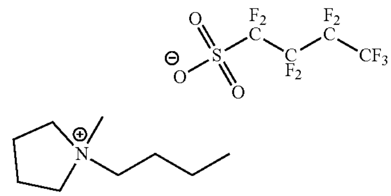 | 21.2 ± 0.5 | 146 ± 1 | 103.4 ± 0.8 |

It is to be noted here that the oxygen concentration is highest for ILB, and the latter ionic liquid therefore appears to be of particular interest. An increase in O$_2$ concentration, and low volatility, are advantages associated with the use of this ionic liquid.

Further, ionic liquid IL C has been made in a new way. In a further aspect, the present invention thus relates to a method of synthesis of N,N-butylmethylpyrrolidinium nonafluorobutanesulfonate comprising the step of reaction of N,N-butylmethylpyrrolidinium chloride with lithium nonaflate in a solvent, such as dichloromethane, preferably room temperature. The solid residue (LiCl) may be filtered off and the solvent evaporated, these steps being repeated to prepare purified product. There are various advantages in this approach (especially for potential scale-up of the synthesis):
1) Time: only 1 h of reaction time;
2) Temperature: reaction at room temperature;
3) Purification of the organic layer via precipitation;
4) High yield (88%).

The invention claimed is:

1. Ionic compound containing an anion, and a cation having the following structural formula (1):

$$R^1R^2R^3N^+\text{-(linker}^1\text{)-O-(linker}^2\text{)-(FC)} \quad (1)$$

wherein:
R$^1$ and R$^2$ either 1) are both C1-C6 linear or branched alkyl groups, or 2) together form a N-heterocylic ring with the nitrogen atom to which they are joined;
R$^3$ is a C1-C6 linear or branched alkyl group;
the linker$^1$ consists of: an alkylene chain —(CH$_2$)$_n$— wherein n≥1, or a chain of formula —(CH$_2$—O—CH$_2$—)$_p$ wherein p≥1;
the linker$^2$ consists of an alkylene chain —(CH$_2$)$_m$— wherein m≥1, or a chain of formula —(CH$_2$—O—CH$_2$—)$_q$ wherein q≥1;
the group FC is a fluorinated alkyl group of formula C$_a$H$_b$F$_c$ wherein b+c=2a+1, where c is at least 1 and at most 2a+1 and where a is at least 1 and at most 10;
with the proviso that when linker$^2$ consists of an alkylene chain —(CH$_2$)$_m$—, -(linker$^2$)-(FC) has a chain length of greater than 5 carbon atoms.

2. Ionic compound according to claim 1, wherein R$^1$R$^2$ together form a ring with the nitrogen atom to which they are joined, and the ring is chosen from the group consisting of: pyrrolidine, piperidine, imidazole, pyridine and morpholine, and wherein for any of these ring types, one or more substituent groups may be present on the ring, the substituent groups being chosen from the group consisting of: halo, alkyl, and aryl groups.

3. Ionic compound according to claim 2, wherein R$^1$R$^2$ together form a ring with the nitrogen atom to which they are joined, and the ring is a pyrrolidine or piperidine ring, and wherein for either of these ring types, one or more substituent groups may be present on the ring, the substituent groups being chosen from the group consisting of: halo, alkyl, and aryl groups.

4. Ionic compound according to claim 1, wherein in linker$^1$:
n is at most 10;
p is at most 5;
and in linker$^2$:
m is at most 10;
q is at most 5.

5. Ionic compound according to claim 1, wherein the linker group linker$^1$ is ethylene —CH$_2$—CH$_2$—.

6. Ionic compound according to claim 1, wherein the linker group linker$^2$ is methylene —CH$_2$—.

7. Ionic compound according to claim 1, wherein c>b in the fluorinated alkyl group FC.

8. Ionic compound according to claim 1, wherein the anion is one or more chosen from the group consisting of: C$_n$F$_{2n+1}$—SO$_2$—N—SO$_2$—C$_m$F$_{2m+1}^-$, PF$_6^-$, BF$_4^-$, C$_n$F$_{2n+1}$COO$^-$ and C$_n$F$_{2n+1}$SO$_3^-$; where n and m are at least 1 and at most 10.

9. Electrolyte material comprising an ionic compound according to claim 1, and a metal salt.

10. Electrolyte material according to claim 9, wherein the metal salt is a lithium (Li) salt.

11. Metal-air battery using an electrolyte material according to claim 9.

12. Ionic compound containing an anion, and a cation having the following structural formula (1):

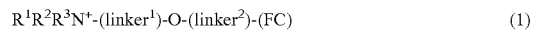

wherein:
R$^1$ and R$^2$ either 1) are both methyl or ethyl, or 2) together form a N-heterocylic ring with the nitrogen atom to which they are joined;
R$^3$ is a methyl or ethyl;
the group FC is a fluorinated alkyl group of formula C$_a$H$_b$F$_c$ wherein b+c=2a+1, where c is at least 1 and at most 2a+1 and where a is at least 1 and at most 10,
the linker group linker$^1$ is ethylene —CH$_2$—CH$_2$—, and
the linker group linker$^2$ is methylene —CH$_2$—;
with the proviso that -(linker$^2$)-(FC) has a chain length of greater than 5 carbon atoms.

* * * * *